United States Patent
Peterson et al.

(10) Patent No.: US 9,824,492 B2
(45) Date of Patent: Nov. 21, 2017

(54) HOLLOW OBJECT MODEL VISUALIZATION IN MEDICAL IMAGES

(71) Applicant: Vital Images, Inc., Minnetonka, MN (US)

(72) Inventors: Samuel W. Peterson, Topanga, CA (US); Pascal Salazar-Ferrer, Eden Prairie, MN (US); Yan Yang, Eden Prairie, MN (US)

(73) Assignee: Vital Images, Inc., Minnetonka, MN (US)

( * ) Notice: Subject to any disclaimer, the term of this patent is extended or adjusted under 35 U.S.C. 154(b) by 0 days.

(21) Appl. No.: 15/080,246

(22) Filed: Mar. 24, 2016

(65) Prior Publication Data

US 2017/0278301 A1   Sep. 28, 2017

(51) Int. Cl.
| | |
|---|---|
| *G06T 17/10* | (2006.01) |
| *G06F 19/00* | (2011.01) |
| *G06T 19/20* | (2011.01) |
| *G06T 15/08* | (2011.01) |
| *G06T 19/00* | (2011.01) |
| *G06T 17/00* | (2006.01) |

(Continued)

(52) U.S. Cl.
CPC ............ *G06T 17/10* (2013.01); *G06F 19/321* (2013.01); *G06T 15/08* (2013.01); *G06T 17/005* (2013.01); *G06T 19/003* (2013.01); *G06T 19/20* (2013.01); *G05B 19/4097* (2013.01); *G05B 19/4099* (2013.01); *G06T 2219/2021* (2013.01)

(58) Field of Classification Search
CPC ...... G06T 17/00–17/30; G06T 2210/41; G05B 19/4097; G05B 19/4099
See application file for complete search history.

(56) References Cited

U.S. PATENT DOCUMENTS

| | | | |
|---|---|---|---|
| 2003/0074174 A1* | 4/2003 | Fu | ................ G05B 19/4099 703/13 |
| 2011/0093243 A1 | 4/2011 | Tawhai et al. | |

(Continued)

OTHER PUBLICATIONS

Meshmixer Video Tutorial Titled "mm08 thicken/shell tutorial", dated Feb 1, 2013, available at: https://www.youtube.com/watch?v=ILKspBZjSDM, and select screenshots.*

(Continued)

*Primary Examiner* — Daniel Hajnik
(74) *Attorney, Agent, or Firm* — Schwegman Lundberg & Woessner, P.A.

(57) ABSTRACT

Techniques for generating a hollow model from a medical image are disclosed herein. In an example, a hollow model may be created within a medical imaging visualization application through the generation of a mask of an interior space of a segmented anatomical structure, the extrusion of a shell mask from the mask of the interior space, and the generation of a visualization of the shell mask within the medical imaging visualization application. For example, the mask may be provided as a layer in the medical imaging visualization application, allowing a user to visualize the produced shell mask of the hollow model from the perspective of the medical imaging. In further examples, the hollow model generation techniques may be used with techniques for shell region modifications, variable shell thickness, multiple shell layer, and trimming of shell endpoints.

21 Claims, 18 Drawing Sheets

(51) Int. Cl.
  *G05B 19/4097* (2006.01)
  *G05B 19/4099* (2006.01)

(56) References Cited

U.S. PATENT DOCUMENTS

| | | | |
|---|---|---|---|
| 2011/0205583 A1 | 8/2011 | Young et al. | |
| 2012/0041318 A1 | 2/2012 | Taylor | |
| 2012/0203530 A1 | 8/2012 | Sharma et al. | |
| 2013/0345794 A1 | 12/2013 | Khatiwala et al. | |
| 2014/0031967 A1* | 1/2014 | Unger | B29C 67/0088 700/119 |
| 2015/0104090 A1 | 4/2015 | Hopfgartner et al. | |
| 2015/0269351 A1 | 9/2015 | Taylor et al. | |
| 2015/0342720 A1 | 12/2015 | Koc et al. | |
| 2016/0129640 A1* | 5/2016 | Yamazaki | B29C 67/0088 700/119 |
| 2016/0136883 A1* | 5/2016 | Schmidt | B29C 67/0088 264/129 |

OTHER PUBLICATIONS

Bremer, Peer-Timo, et al. "Virtual clay modeling using adaptive distance fields." Proceedings of the 2002 international conference on imaging science, systems, and technology (CISST 2002). vol. 8, 2002.*

"MeshLab", [Online]. Retrieved from the Internet: <URL:http://meshlab.sourceforge.net/, (Apr. 2, 2014), 1-8.

"Meshmixer 3.0", [Online]. Retrieved from the Internet: <URL: http://www.123dapp.com/meshmixer, (Nov. 10, 2015), 1-8.

Cignoni, P., et al., "MeshLab: an Open-Source Mesh Processing Tool", Eurographics Italian Chapter Conference 2008, (2008), 129-136.

Duan, Bin, et al., "3D Bioprinting of Heterogeneous Aortic Valve Conduits with Alginate/Gelatin Hydrogels", J Biomed Mater Res A 101 (5), (May 2013), 1255-1263.

Guo, Xiaomei, "Diameter-dependent axial prestretch of porcine coronary arteries and veins", J Appl Physiol 112, (2012), 982-989.

Hockaday, L. A., et al., "Rapid 3D printing of anatomically accurate and mechanically heterogeneous aortic valve hydrogel scaffolds", Biofabrication 4, (Aug. 23, 2012), 12 pgs.

Kolesky, David B., "3D Bioprinting of Vascularized, Heterogeneous Cell-Laden Tissue Constructs", Advanced Materials, 26, (2014), 3124-3130.

Kucukgul, Can, et al., "3D Bioprinting of Biomimetic Aortic Vascular Constructs With Self-Sopporting Cells", Biotechnology and Bioengineering, vol. 112, No. 4, (Apr. 2015), 811-821.

Kucukgul, Can, et al., "3d hybrid bioprinting of macrovascular structures", Procedia Engineering 59, (2013), 183-192.

Montaudon, M., et al., "Assessment of bronchial wall thickness and lumen diameter in human adults using multi-detector computed tomography: comparison with theoretical models", J. Anat. 211, (2007), 579-588.

Podesser, B. K., "Outer Radius-Wall Thickness Ratio, a Postmortem Quantitative Histology in Human Coronary Arteries", Acta Anatomica, 163, (1998), 63-68.

Schmidt, Ryan, et al., "Meshmixer: an interface for rapid mesh composition", (2010), 1 pg.

"European Application Serial No. 17160713.8, Communication Pursuant to EPC Ru 69 dated Oct. 2, 2017", 2 pgs.

"European Application Serial No. 17160713.8, Extended European Search Report dated Aug. 18, 2017", 13 pgs.

Chandru, Vijay, et al., "Voxel-based modeling for layered manufacturing", IEEE Computer Graphics and Applications., vol. 15, No. 6, XP055395749, ISSN: 0272-1716, DOI: 10.1109/38.469516, (Jan. 1, 1995), 42-47.

Kurenov, Sergei N, et al., "Three-demensional printing to facilitate anatomic study, device development, simulation, and planning in thoracic surgery", Journal of Thoracic and Cardiovascular Surgery. vol. 149, No. 4, XP055302959, ISSN: 0022-5223, (Apr. 1, 2015), 973-979.

Mark, Forsyth, et al., "Shelling and offsetting bodies", Proceedings of the Third Symposium on Solid Modeling and Applications, Salt Lake City, May 17-19, 1995; [Proceedings of the Symposium on Solid Modeling and Applications], New York, ACM, US, (Dec. 1, 1995), 373-381.

Mary, Ann Liebert, et al., "3D -Printed Tissue -Mimicking Phantoms for Medical Imaging and Computational Validation Applications", XP055122172, DOI: 10.1089/3dp.2013.0010, [Online] retrieved from the internet: <:http://online.liebertpub.com/doi/pdf/10.1089/3dp.2013.0010>, (Jan. 1, 2014).

Tarjuelo-Gutierrez J, et al., "High-quality conforming hexahedral meshes of patient-specific abdominal aortic aneurysms including their intraluminal thrombi", Medical & Biological Engineering & Computing, XP055130071, DOI: 10.1007/S11517-013-1127-5, [Online] retrieved from the internet: <http: //search. proquest. com/docvi ew/1491042937>, (Feb. 1, 2014), 159-198.

* cited by examiner

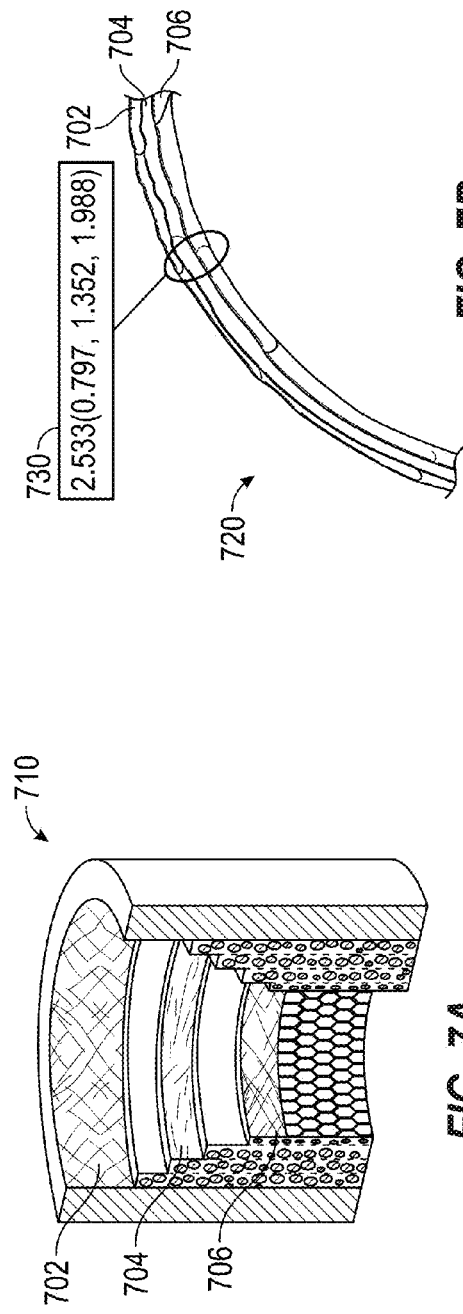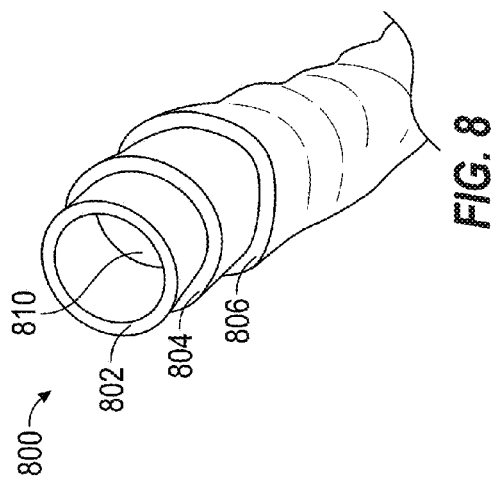
FIG. 7A
FIG. 7B
FIG. 8

HOLLOW OBJECT MODEL VISUALIZATION IN MEDICAL IMAGES

TECHNICAL FIELD

Embodiments pertain to techniques and systems for displaying images obtained from medical imaging procedures. Further embodiments relate to visualization techniques used for generating models of anatomical structures in medical images displayed via medical imaging viewer software applications.

BACKGROUND

Medical imaging visualization software may be used to perform segmentation of organs and other anatomical structures and features from images of a human subject. After performing the segmentation of an organ, for example, a model of the interior hollow structure of an anatomical feature within the organ may be desired. Although the "empty" space of hollow structures can be segmented and visualized in software, a medical professional may desire that a model of the hollow structure be generated and visualized separately. These models, referred to as "hollow models", may be used to model hollow anatomical features such as vessels, lung airways, and heart chambers.

Hollow models are useful for physically modelling fluid flow and the internal structure of the subject organ, among other objectives. To allow the depiction of the internal structure in a real-world space, a "shell" can be defined and indicated around the otherwise hollow, empty space of the model cavity. For example, a medical professional may wish to print a three-dimensional perspective of the hollow structure within an organ using a 3-D printer, to represent the true biological structures surrounding the organ's interior empty space.

BRIEF DESCRIPTION OF THE DRAWINGS

FIGS. 7A and 7B illustrate respective layers of an anatomical structure used for defining variable thicknesses of a multi-layer region shell for a hollow model according to an example described herein.

FIG. 8 illustrate a graphical depiction of multi-layer region shell generated for a hollow model according to an example described herein.

DETAILED DESCRIPTION

Figure 1:
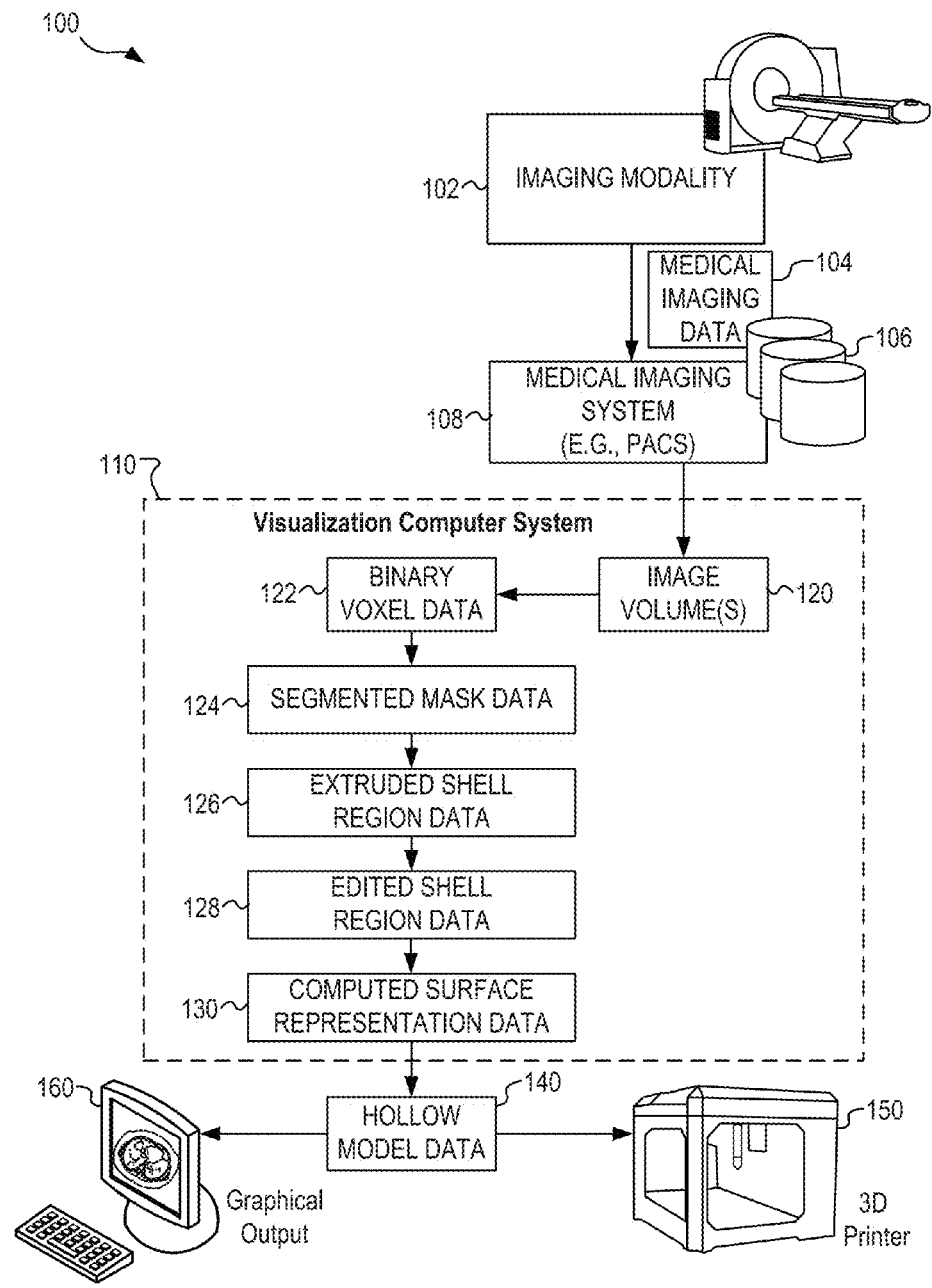
FIG. 1 illustrates a block diagram of a system configuration for generating hollow model data with use of a medical imaging visualization computer system according to an example described herein.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

The present disclosure illustrates various techniques and configurations that enable the creation of a hollow region model surrounding a three-dimensional (3D) source region within a medical imaging 3D dataset. These techniques allow a user of a medical imaging visualization software to extract a shell of a desired thickness around a solid region prior to surface creation and export of the shell from the visualization software. The extraction of this shell constitutes a step within the segmentation process itself because the output of the step is, in turn, another segmented region within a space modelled within the visualization software. The resulting shell of the hollow model can be previewed with the original 3D image within the visualization software, modified within the visualization software, and further exported to be used in various applications such as 3D visualization, 3D printing, bioprinting, or computer simulations.

With the use of the present techniques, a user may interact with and visualize a shell of a hollow model within a medical imaging visualization software application in the same way that interaction and visualization occurs for other segmented objects and regions. In addition, the presence of volumetric context information within the medical imaging visualization software allows various extensions and enhancements of the shell to be selected, presented, and implemented in a computationally efficient manner. As a result, the model data generated for hollow models of anatomical structures and features such as vessels, heart chambers, and airways may be generated and visualized in an enhanced manner.

In a further example, the presently disclosed techniques may be used with enhancements to the generation or modification of a hollow model, including a feature to implement clipping of a tree structure produced from a hollow model (such a tree structure produced from a hollow model of vascular anatomy). This clipping technique may utilize morphological information to assist a user in quickly trimming away distal tree endpoints of a hollow model, to produce a shell that provides key structure of the hollow model while providing visibility into the interior structure (that is particularly useful for 3D printed output of the hollow model).

In a further example, the presently disclosed techniques may be used with other enhancements to the generation or modification of a hollow model, including a feature to implement constrained region shell generation for a hollow model. For example, defining and growing a region shell around an existing source region may generate unwanted results if the new 3D region for a shell of a hollow model is generated to grow into another, existing region. The shell generated for the hollow model may be customized to adapt to this scenario and to preserve the integrity of neighboring anatomical features, thus providing a more accurate simulation and modeling of the real-world anatomical structure.

In a further example, the presently disclosed techniques may be used with other enhancements to the generation or modification of a hollow model, including with a feature to implement variable region shell thickness for a hollow model. Such variable thickness may allow a generated region shell to vary according known relationships between the local geometry of the source region and the local geometry of the region shell. For example, the variable thickness may be determined from defined anatomic relationships of wall thickness (shell thickness) with the inner diameter of the anatomical structure (the hollow space within the model) for anatomy such as airways or coronaries.

In a further example, the presently disclosed techniques may be used with other enhancements to the generation or modification of a hollow model, including with a feature to implement a multilayer region shell for a hollow model. For example, a generated region shell may be modeled to include a plurality of layers (contiguous embedding 3D regions) for its shell mask, with the thicknesses of respective layers being established from respective user-specified values or system-default values correlating to the segmented anatomical structure. This may allow a generated region shell (that might otherwise be made of a single thickness) of a hollow model to simulate a multi-layer vascular structure, again to provide a more accurate simulation and modeling of the real-world anatomical structure.

FIG. 1 illustrates a block diagram of a system configuration 100 for generating hollow model data 140 with use of a medical imaging visualization computer system 110 according to an example. It will be understood that the following system configuration 100 is illustrated as an example, and individual features of the following medical imaging and imaging processing components may be integrated or separated among various machines, systems, and devices. Further, many of the segmentation and computation functions depicted in the following example may be simulated or replicated by like functions within consolidated or separated device subsystems.

As illustrated in the system configuration 100, medical imaging data 104 (including three-dimensional image data) of a human subject is acquired from an imaging modality 102 such as a computed tomography (CT), magnetic resonance imaging (MRI), 3D X-ray angiography, or 3D ultrasound modality. The medical imaging data 104 may be maintained, stored, or persisted in a database 106 of a medical imaging system 108 such as a picture archiving communication system (PACS), although the present techniques may be used in combination with other image data retrieval, caching, or storage systems. The format of the electronic data produced by the imaging modality 102 may be in a proprietary or industry standard format, such as in a Digital Imaging and Communications in Medicine (DICOM) format, which may be further processed or consolidated by the medical imaging system 108.

The medical imaging data 104 is processed by the visualization computer system 110 to extract or generate one or more image volumes 120 that provide data representations of 3D anatomic structures such as blood vessels, pulmonary airways, and cardiac chambers. These anatomic structures may be segmented from one or more image volumes 120 generated or produced from the original image content of the medical imaging data 104. The one or more image volumes 120 may be further processed by the visualization computer system 110 to generate binary voxel data 122 of an area of interest, including in response to user selections or automated identification of an area of interest in a graphical user interface (including through the application of automated or user-controlled segmentation techniques).

The binary voxel data 122 may be processed by the visualization computer system 110, to provide a real-time graphical preview or output of an area of interest. As further depicted with reference to the graphical user interface of FIGS. 3A to 3D, this graphical preview may allow selection and interaction of an area of interest from one or multiple perspectives. The binary voxel data 122 may be further segmented within the visualization computer system 110 to identify a hollow area within the area of interest. As an example, the application of automated or manual segmentation may be used to extract a hollow, inner portion of an area of interest (e.g., vessel lumen, cardiac blood pool, airway lumen, or the like) such as based on the higher contrast identifiable within the medical images. This identification of a segmented portion of a hollow area may be used to produce segmented mask data 124 for the hollow structure.

From the segmented mask data 124, a set of extruded shell region data 126 may be generated within the visualization computer system 110. This extruded shell region data 126 may represent a region shell of a user- or system-defined thickness (or thicknesses). This extruded shell region data 126 may be visualized within the within the visualization computer system 110 as a segmented layer, including as a visualization within other two- or three-dimensional views of medical images. The extruded shell region data 126 may be modified to produce edited shell region data 128, such as with the application of various extensions and modifications as further discussed herein (including one or more of the enhancements discussed with reference to FIGS. 4A to 9) to adjust the thickness, shape, layering, and endpoints of the region shell.

As a result of the extruded shell region data 126 and any editing to produce the edited shell region data 128, computed surface representation data 130 may be produced in the visualization computer system 110 (including as direct visualization outputs from the visualization computer system 110). This computed surface representation data 130 may be exported as hollow model data 140 that represents the shell for the hollow model. For example, the hollow model data 140 may be exported for output with a 3D printer

150 to generate various real-world physical models; the hollow model data 140 may also be exported to a graphical output 160 for use with other 3D visualization applications. The hollow model data 140 may be exported in the form of a mesh model, such as a .stl (stereolithography) computer aided design (CAD) mesh model, that can be further used with CAD software and machines.

Thus, the hollow model data 140 may be exported for uses such as 3D visualization, 3D printing, bioprinting of biomimetic or vascularized tissues, and like physical simulations. Such uses are common with hollow models surrounding anatomical structures because they can represent the true biological structures (e.g. airway or vessel walls) that are being evaluated. Hollow models also offer a superior visualization of the internal cavities (e.g. cardiac chambers) while using less printing materials than a model of an entire organ or anatomical structure. Accordingly, hollow model data 140 exported with the present techniques provide superior uses for analyzing lung airway walls, or the vessel wall surrounding a vessel tree such as the coronary tree or the aorta.

Other techniques that are used to generate a hollow model in software and define the shell for such a hollow model often involve extensive user interaction and input. For example, some techniques to create a hollow model may involve the use of mesh manipulation after a user extracts a hollow object surface model from an initial solid mesh. To create this mesh model, a user would first segment the features of the hollow model in a medical image visualization software program, export the segmented hollow model features from the visualization software program to a separate computer aided design program, perform the mesh manipulation, and then provide extensive user input to manually define the artificial shell structure around the space of the hollow structure.

Such techniques for extruding or hollowing out an object after it has been converted to a surface representation provide disadvantages and technical issues that are resolved by use of the presently disclosed techniques. For example, existing techniques may generate a 3D mesh model defining the surface of the reference structure (e.g. a vessel lumen) in a compatible file format such as .stl, .obj., .zpr, and perform an extrusion at some specified thickness from the initial mesh model to generate a hollow object (e.g. the vessel wall). Mesh model manipulation tools then may allow a user to extract a hollow object surface model from this model through extrusion. However, this type of a technique results in various issues, including:

Absence of context: The original context data from the original medical image is often not present or perceivable by within the mesh manipulation software. The presently disclosed techniques provide the benefit of being able to visualize (and potentially modify) the hollowed-out result within the visualization software, preserving the context of the original image data from which the anatomical region was segmented.

Topological issues: Topological anomalies can be problematic when working directly with the surface. For instance, when disparate portions of the object's boundary are within a distance less than the extrusion thickness, there may be a collision of surfaces that can be difficult to resolve. This may also affect neighboring structures that may need to be factored into the resulting shell. The presently disclosed techniques provide the benefit of being able to identify collisions in the larger context of the source medical data and the visualization application, and modify the shape or thickness of the resulting hollow model shell to mitigate the effect of such collisions.

Software efficiency: The tool(s) and/or software used for working with region shells are often different from those for working with surface meshes. Thus, if the user needs to post-process a mesh simply to extrude a hollowed-out model, then the user will likely need to learn and adjust to a new tool for doing so. Additionally, to modify the hollowed out model based on the 3D anatomical images, the user may have to reimport the model in the original software. The presently disclosed techniques allow creation, modification, and export capabilities to be generated directly within the visualization software, automating certain operations, reducing the complexity of operations, and reducing the amount of data that is exchanged among software applications.

Endpoint output: Closed endpoints may be present in the model that lead to unintended forms of the shell, particularly with a 3D printer generation of tree-based anatomical structures. In order for the final hollow object of such structures to be properly printed, the structure must be cut open in one or more locations. For vessel and airway models, this would typically be done at the proximal and distal ends of the vascular tree, often involving a tedious, manual process of rotating the model and then sculpting away tips of the structure at various endpoints. The use of the present techniques may reduce such operations through the use of user-directed and automated features that can identify and trim endpoints, and identify issues with a hollow model directly within the medical image visualization platform.

Figure 2:
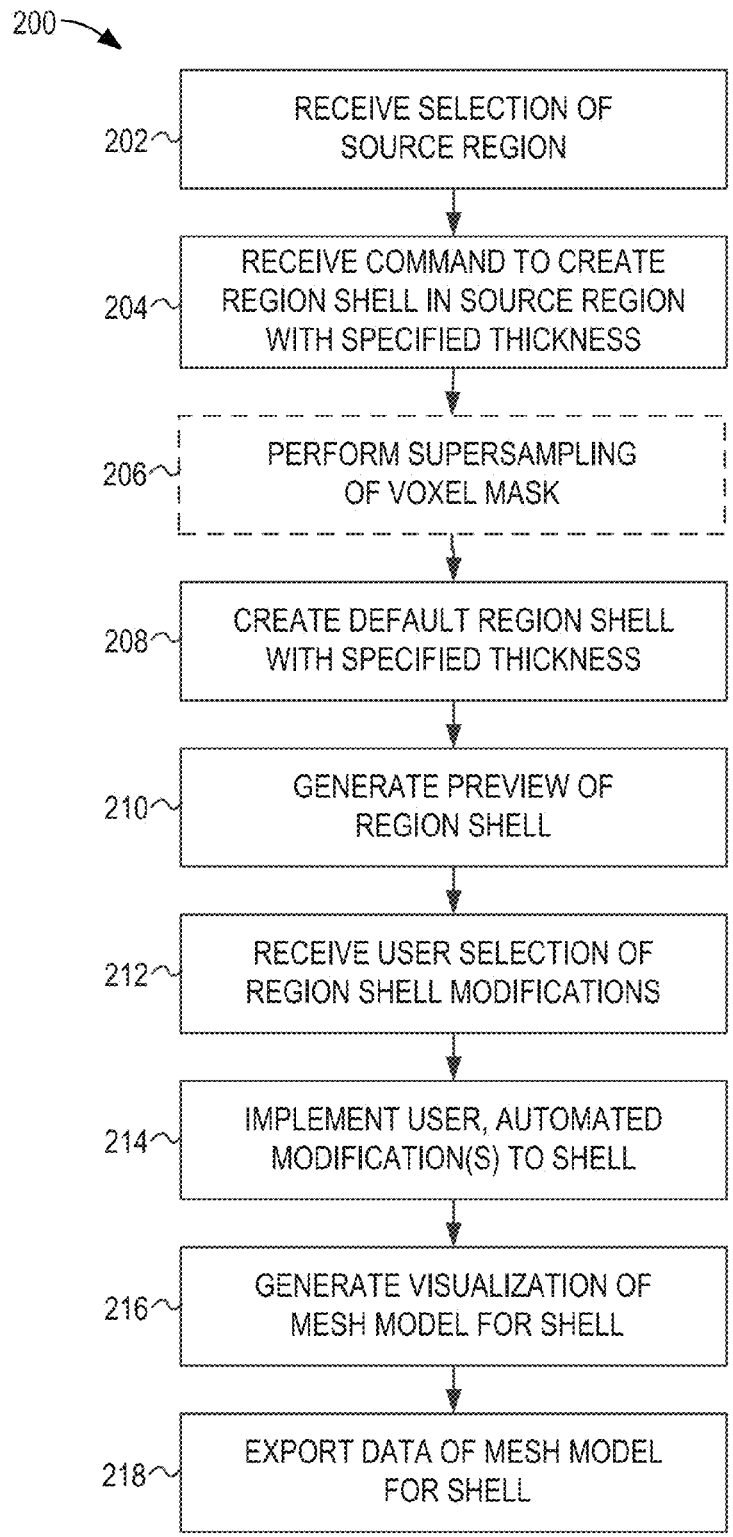
FIG. 2 illustrates a flowchart of an example method for generating and outputting hollow model data according to an example described herein.

FIG. 2 illustrates a flowchart 200 of an example method for generating and outputting hollow model data according to an example described herein. This flowchart 200 provides a detailed example from the perspective of a computing system and software configured to receive and respond to user interaction, such as from visualization software operating on the visualization computer system 110. It will be understood, however, that these operations may be distributed among multiple computer systems or devices (including systems under the control or direction of user inputs).

First, the visualization software may operate to receive a selection of a source region (operation 202), such as the selection of a segmented object or anatomical feature. The visualization software may operate to receive a command to create a region shell in the source region (operation 204) from the segmented object or anatomical feature. This region shell may be created (operation 208) with the use of a binary voxel mask for a desired thickness t (e.g., a thickness value specified by the user or determined by the visualization software), including in some examples the use of supersampling upon the voxel mask (operation 206).

The visualization software may operate to generate a preview of the region shell (operation 210) for output to the user in a user interface of the visualization software. The visualization software may further operate to receive user selections of region shell modifications within the user interface (operation 212), such as user selections for thickness, layer, and endpoint modifications of the shell, and to implement these modifications to the shell (operation 214).

Based upon the user and automated modifications to the shell and other algorithmic processing, the visualization software operates to extrude and output a visualization for a mesh model of the shell (operation 216) and generate data for the mesh model of the shell (operation 218). This data for the mesh model may be exported for further visualization in a computer aided design program, exported to a 3D printer for printing, or like uses for a 3D representation of the shell.

Extrusion, as used herein, refers to a technique for creating a three-dimensional model from segmented 3D hollow anatomical structures of source medical imaging data and extending the profile (e.g., expanding the profile) of such hollow anatomical structures to a defined depth. The defined depth of the hollow model shell is referred to herein as the thickness. The result from the extrusion is a 3D visualization of the profile, which may be visualized and exported to a wireframe or mesh model as discussed above. In an example, the source medical imaging data provides a 3D voxel mask of the hollow anatomical structure from the one or more image volumes (e.g., the DICOM image data); in another example, the source imaging data provides contour data of the hollow anatomical structure from the one or more image volumes.

In an example, the visualization software may operate to extrude a shell of desired thickness, constrained by the voxel granularity, by dilating the original binary voxel mask and then removing the original voxel mask from the dilated result. The operations to extrude the shell may be performed using supersampling to allow an increased granularity of the shell thickness. As an example, supersampling may be performed upon voxels of a first resolution (e.g., voxels of a 1 mm resolution) in order to generate a second, finer resolution for use in the extruded shell (e.g., voxels used in a layer thickness of 0.5 mm). Trilinear or tricubic interpolation may be used to supersample the binary region mask in order to reduce aliasing artifacts in the resulting structure and yield a smoother surface model if one is ultimately extracted. In order to prevent collisions with other structures, binary masks for other anatomy may be (a) removed from the shell mask (if they are fixed), or (b) updated to exclude the shell (if they are not fixed). Furthermore, the created shell may be provided as a manipulable region within the visualization software, and thus may be merged with other regions or edited with tools provided by the visualization software for other regions.

In an example, the generation of the region shell may be performed within the visualization software as a specialized segmentation operation. For example, given a binary voxel mask, M and a desired thickness t, the following algorithm may be performed to generate a hollow object shell from mask M:

1. Compute a dilated mask $M^{+t}$ (with supersampling, if applicable) by applying a constant dilation kernel of radius t at all voxels in M.
2. Compute $M_{shell} = M^{+t} - M$.
3. Adjust shell to remove any fixed external structures: $M_{shell} = M_{shell} - M_{fixed}$
4. Adjust any non-fixed external structures to remove $M_{shell}: M_{nonfixed} = M_{nonfixed} - M_{shell}$ In another example, a hollow object shell may be generated within the visualization software from a centerline-enumerated set of an inner and an outer contour of an anatomical structure, such as from contours obtained from cross-sectioning of a hollow segmented hollow anatomical structure. For example, a surface model of the hollow object shell may be extracted from the inner and outer counters of an identified, segmented hollow anatomical structure. The extent of the extracted surface model may be defined from a dilation of the inner contour or from anatomical information within the three-dimensional medical imaging data. Use of such contour information may be useful for generating a realistic representation of the structure, while also permitting automatic endpoint clipping, multi-layered shells, and variable shell thickness, according to the techniques further discussed herein. Additionally, centerline-based editing within the visualization software may directly impact the quality of a resulting shell.

This algorithm and the use of the method of flowchart 200 for generating and outputting hollow model data may be used to extract a shell region in the visualization software, and to produce a shell that envelops a target region prior to surface computation. This enables context to be maintained before the mesh/surface extraction step is performed, even as a user can continue to display the relevant region and segmented structures in the visualization software application.

Figure 3A:
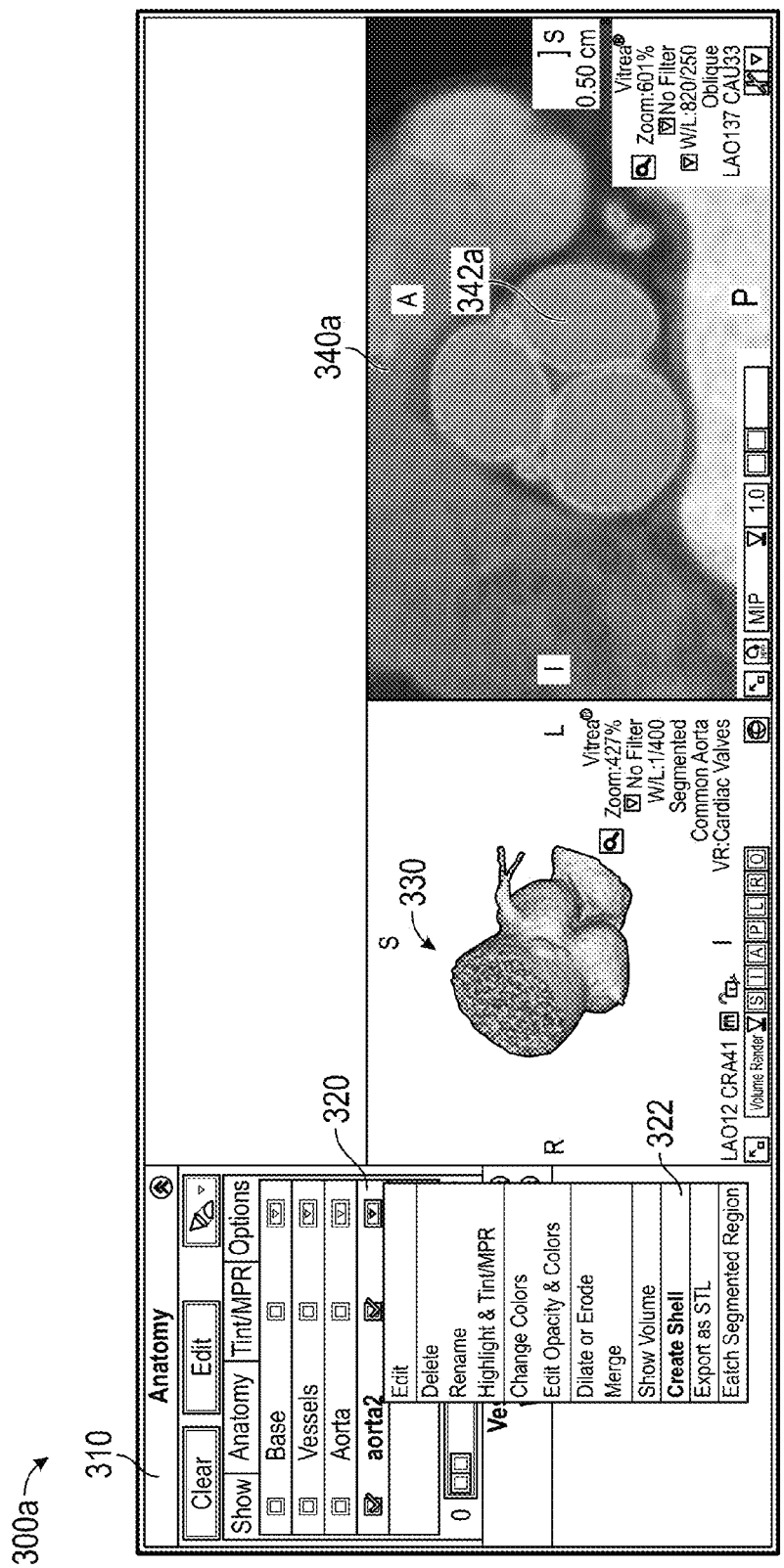
FIGS. 3A and 3B illustrate a graphical user interface of a medical imaging visualization software program configured to select and use a segmentation mask for use in generating a hollow model according to an example described herein.

FIG. 3A illustrates a graphical user interface 300a of a medical imaging visualization software program configured to select a segmentation mask for use in generating a hollow model according to an example. As shown, the graphical user interface 300a includes a listing 310 of anatomical segments, a segmentation layer 320 to visualize a segmented hollow object of an anatomical structure (as depicted, the interior structure of an aorta), a visualization 330 of the segmented hollow object, and an overlay 342a on a two-dimensional medical image 340a depicting a view of the surrounding anatomical structure (as illustrated, a radiology image that denotes the portion of the anatomical structure depicted in the visualization 330).

The graphical user interface 300a depicts a series of further user interface options to be performed upon the segmentation layer 320, including a "Create Shell" menu option 322, in addition to options to show, delete, or modify aspects of the segmentation layer 320. The "Create Shell" menu option 322 may operate as a user-selectable option to create the region shell and to initiate the region shell creation operations discussed above with reference to FIG. 2.

Figure 3B:
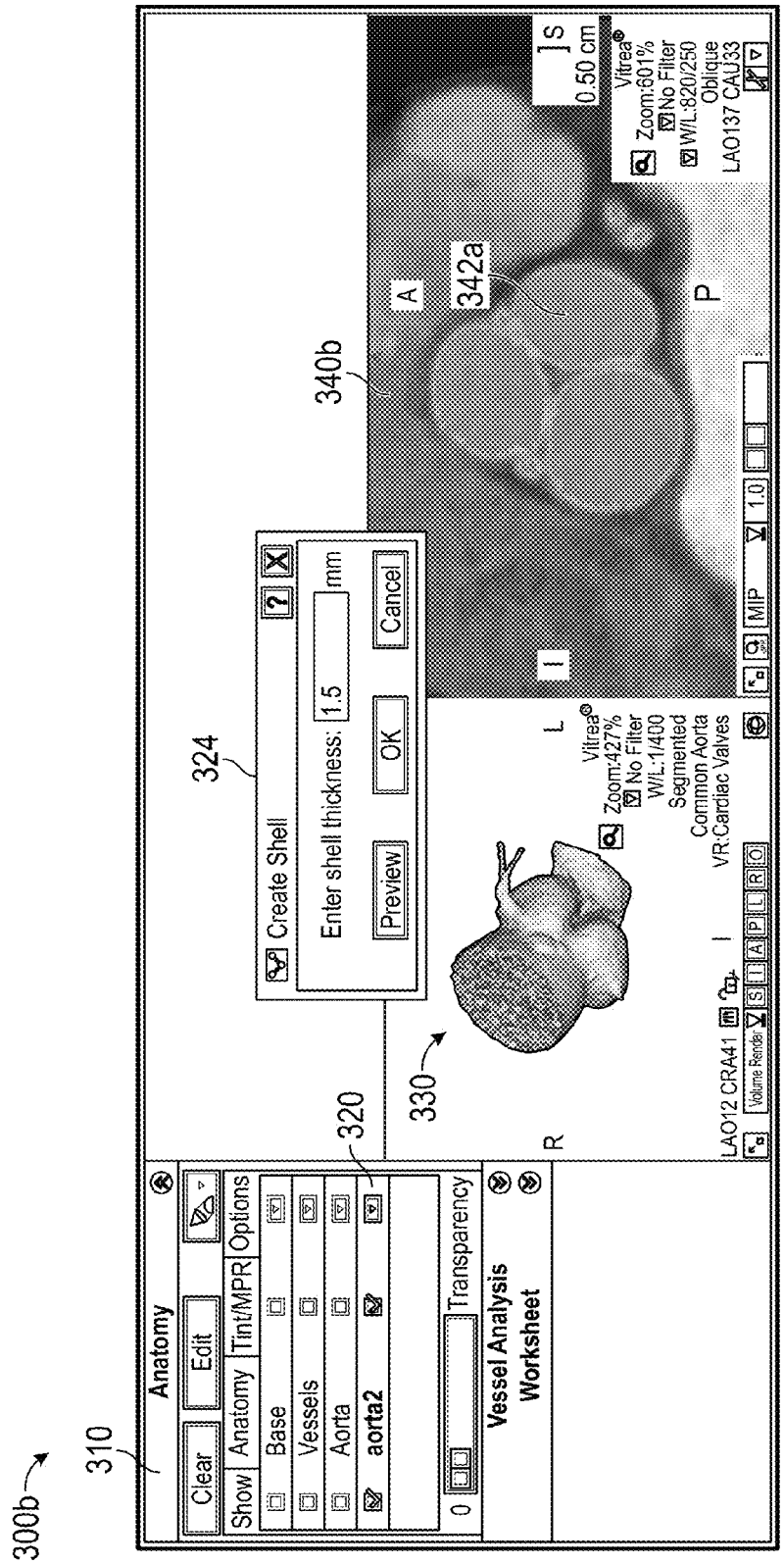

FIG. 3B illustrates a graphical user interface 300b of a medical imaging visualization software program configured to apply a segmentation mask for use in generating a hollow model according to an example. Features of the graphical user interface 300b include those discussed above for the graphical user interface 300a in FIG. 3A.

The graphical user interface 300b depicts a scenario occurring after selection of the "Create Shell" menu option 322, to receive further user interaction. As shown, a user interface input 324 is presented to allow a user to define or modify a shell thickness. The user interface input 324 may include options to apply the defined thickness and to preview the results of the defined thickness. For example, these options may be used to implement operations 204 and 208 in FIG. 2, to create and apply a region shell with a user-specified thickness, and operation 210 in FIG. 2, to generate a preview of the region shell.

Figure 3C:
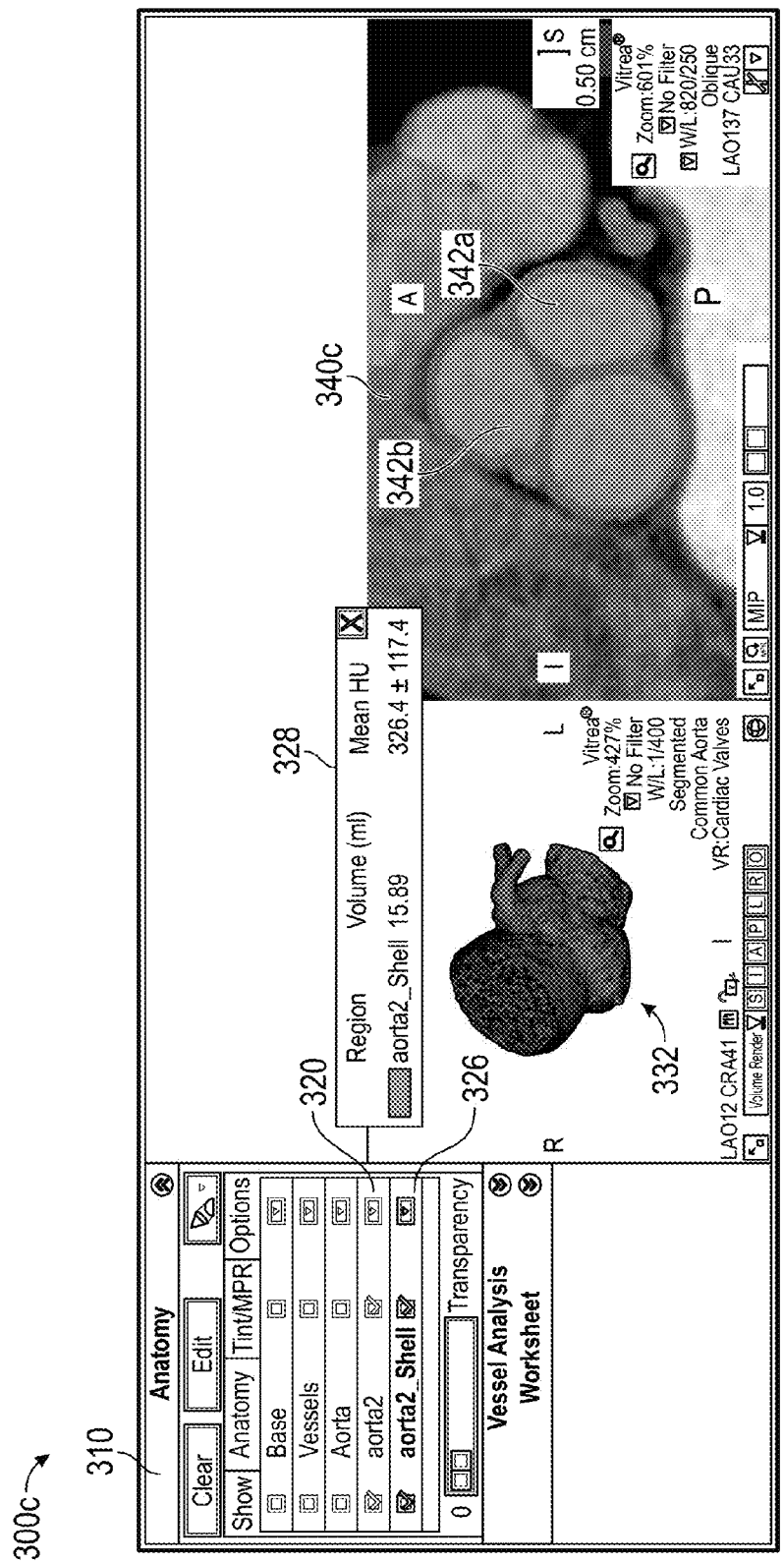
FIG. 3C illustrates a graphical user interface of a medical imaging visualization software program configured to produce an extruded shell region for use in generating a hollow model according to an example described herein.

FIG. 3C illustrates a graphical user interface 300c of a medical imaging visualization software program configured to produce an extruded shell region for use in generating a hollow model according to an example. Features of the graphical user interface 300c include those discussed above for the graphical user interfaces 300a, 300b in FIGS. 3A and 3B.

As shown, the graphical user interface 300c depicts a scenario occurring after entry of the user interface input 324 from FIG. 3B. The hollow object space is used to produce a visualization 332 of the extruded shell region, which is accompanied by a characteristics output 328 of the hollow shell being depicted with the visualization 332. This provides an example of operations 210 and 214 in FIG. 2, to generate a preview of the region shell and to implement modifications to the region shell. The listing 310 of anatomical segments is updated to include a shell segmentation layer 326 in addition to the hollow space represented by the segmentation layer 320.

The graphical user interface 300c also provides an additional overlay 342b within the two-dimensional image 340c of the shell created for hollow structure, in addition to the overlay 342a of the hollow structure. As respective segmentation layers (including the extruded shell region) for the medical image are selected or generated, the visualization software may provide a perspective of the shell relative to the two-dimensional image 340c and other depictions of anatomy.

As shown, the visualization 332 depicts an extracted shell region that envelops the target region prior to surface computation, while maintaining the context and flexibility of working with regions and segmented layers before a mesh/surface extraction step is applied. This shell region is extracted and displayed within the original data context so that it may be visualized and/or modified alongside the source scan data. A 3D and Multiplanar Reconstruction (MPR) preview of the shell within the original data allows the user to accept or modify the shell properties before extruding the new shell region. As a result, the shell may be extracted without topological issues or ambiguities arising from the source region.

Figure 3D:
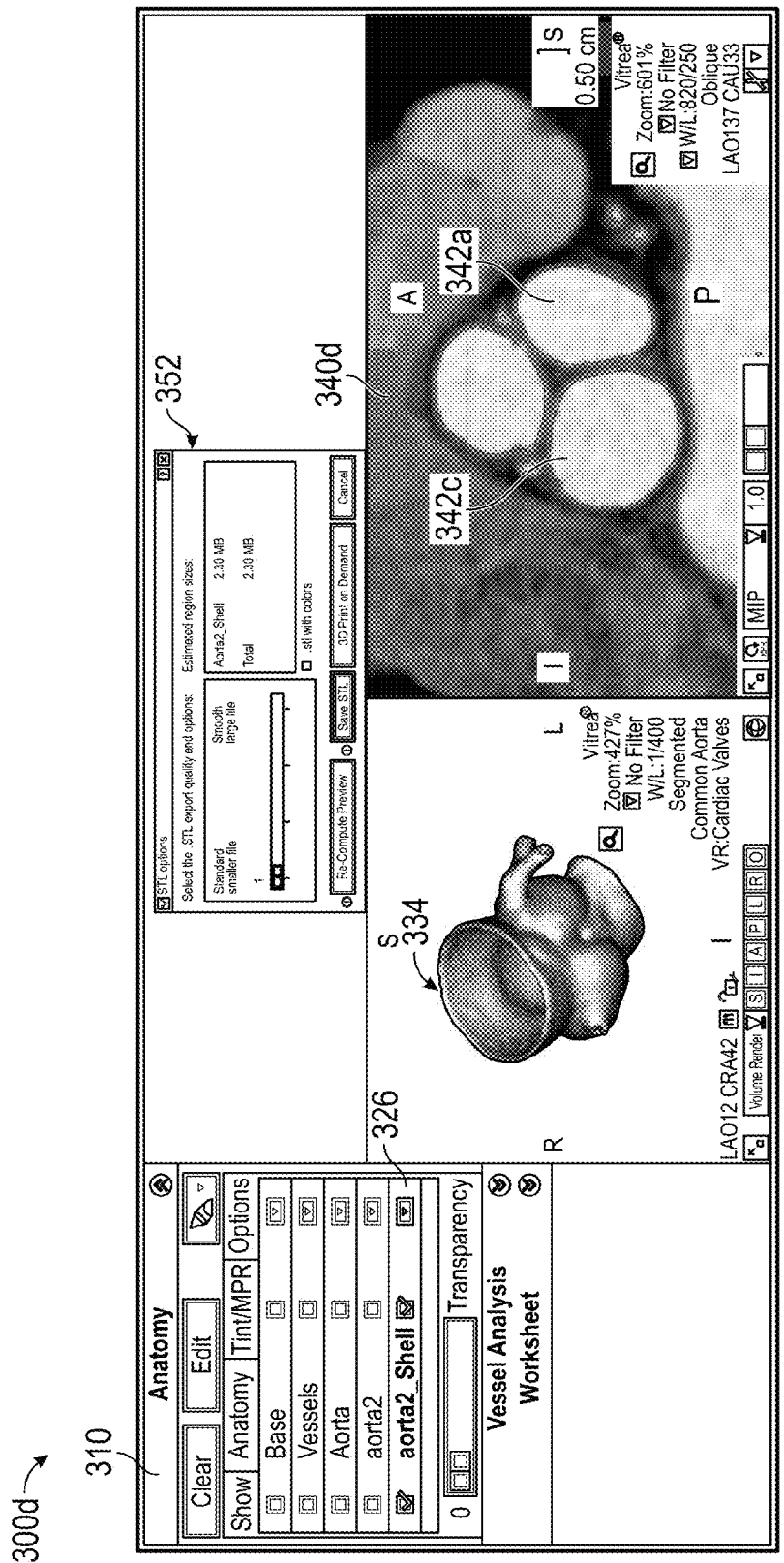
FIG. 3D illustrates a graphical user interface of a medical imaging visualization software program configured to visualize a shell region for use in generating a hollow model according to an example described herein.

FIG. 3D illustrates a graphical user interface 300d of a medical imaging visualization software program configured to visualize a shell region for use in generating a hollow model according to an example described herein. Features of the graphical user interface 300d include those discussed above for the graphical user interface 300a, 300b, 300c of FIGS. 3A, 3B, and 3C.

As shown, the graphical user interface 300d depicts a scenario occurring after selection of a user interface input to remove the hollow structure layer (the segmentation layer 320) and to export the hollow shell (from the shell segmentation layer 326). The hollow region is extruded to produce a visualization 334 of an extruded shell region of the specified thickness, while still presenting features of the shell region in the graphical user interface 300d. An overlay 342c of the shell region is depicted in the two-dimensional image 340d, with a hollow cavity area 342d being omitted in the two-dimensional image 340d. This provides an example of operation 216 in FIG. 2, for generating a visualization of the mesh model for the shell. Further, the graphical user interface 300d may provide an export option interface 352 to directly enable an .STL export of the visualization data.

Figure 3E:
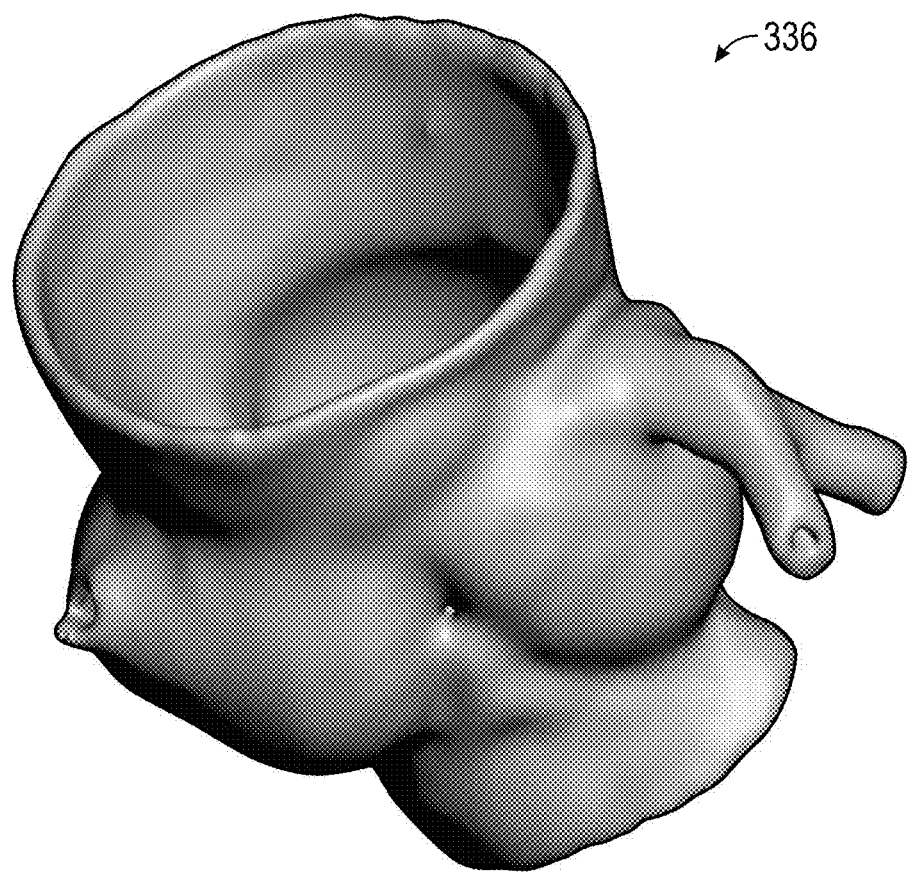
FIGS. 3E and 3F illustrates a graphical visualization and a mesh model for a hollow model produced as an output of a medical imaging visualization software program according to an example described herein.
Figure 3F:
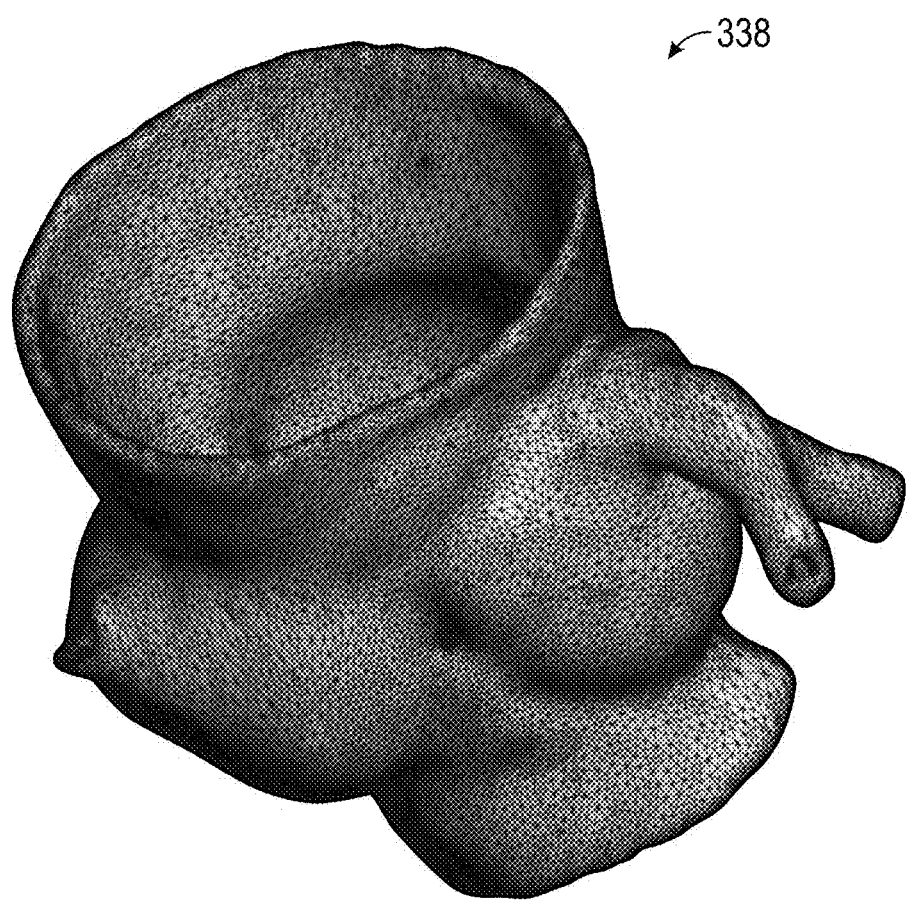

FIGS. 3E and 3F illustrate an enlarged graphical visualization 336 and a mesh model visualization 338 respectively for a hollow model produced as an output of a medical imaging visualization software program according to an example described herein. For example, FIG. 3F provides an example of operation 218 in FIG. 2, of data of a mesh model that is that is exported for a hollow shell. The mesh model may be exported from the graphical visualization 336 of the extruded shell region, for example, and generated into a CAD format.

In addition to the use of 3D printing applications discussed above, 3D hollow models also may be used for medical modelling and simulation. For example, region shells may be defined not only for a physical delineation but also for a clinical justification, such as to define a margin region surrounding a tumor. Accordingly, the generation of the hollow model within may be used for modeling a variety of scenarios, conditions, and environments of human anatomy.

The depiction of the data in FIGS. 3A, 3B, 3C, 3D, 3E, and 3F are provided with reference to the generation and visualization of a hollow model from one image volume. However, in another example, a hollow model may be generated and visualized from data among a plurality of image volumes. For example, multiple image volumes (or series or phases) of three-dimensional imaging data may be used instead of a single volume to perform the generation of the region shell. In this scenario, the source region may be segmented in the multiple volumes, and the shell generation is propagated in each volume. The graphical user interface of the visualization software may include features to allow the selection and depiction of respective volumes for use in generating the hollow shell.

In a further example, the present techniques for generating a hollow model may be combined with automated features for clipping ends of a hollow model for a vascular tree structure. These techniques may utilize morphological information to assist a user in quickly trimming away distal tree endpoints of a previewed hollow model shell. FIGS. 4A, 4B, 4C, and 4D illustrate respective visualizations of a tubular tree structure of a hollow model in a medical imaging visualization interface configured to identify and implement trimming for endpoints of the tree structure according to an example.

Figure 4B:
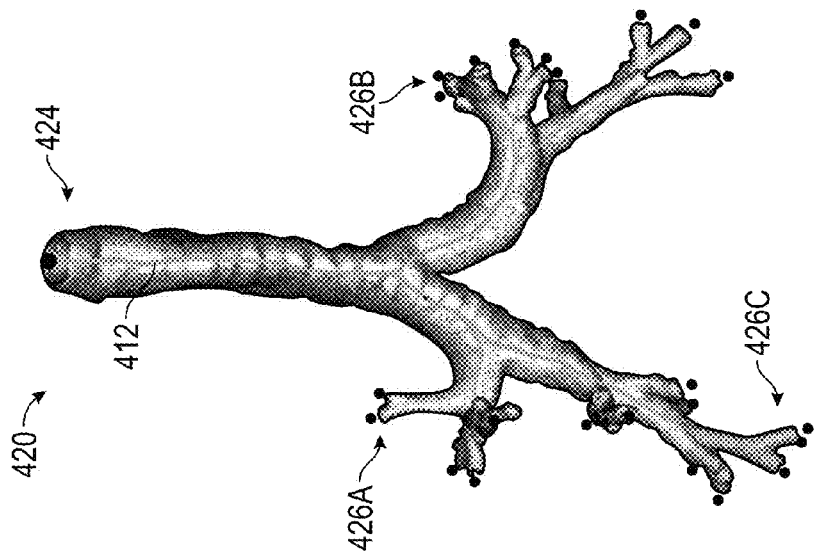
FIGS. 4A, 4B, 4C, and 4D illustrate respective visualizations of a tubular tree structure of a hollow model in a medical imaging visualization interface configured to identify and implement trimming for endpoints of the tree structure according to an example described herein.
Figure 4A:
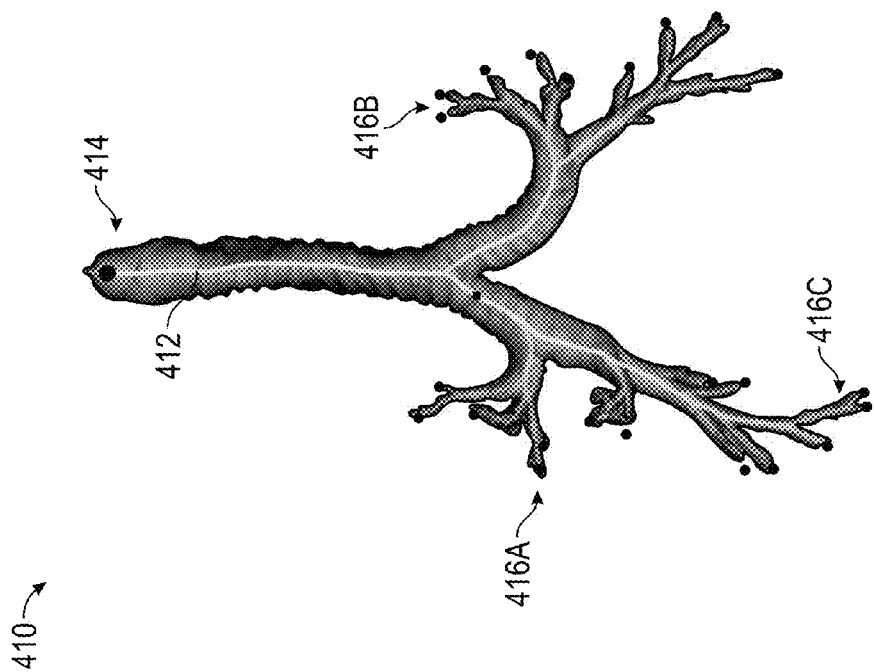

For example, FIG. 4A depicts the illustration of a hollow model 410 generated from the techniques described herein, such as for a hollow model of an airway. As depicted, the hollow model 410 may include a morphological tree branching outline 412 identified within the hollow model 410, with this branching outline 412 (a centerline) extending throughout the hollow model 410. These tree branches may stem to some or all portions of the hollow model 410.

FIG. 4A further depicts the identification of a plurality of endpoints that are automatically detected at the ends of the branching outline 412, such as at endpoints in branches 414, 416A, 416B, 416C. Before trimming, these respective endpoints are closed due to the exterior definition of the hollow shell. However, the tubular structure may be opened for better visualization, phantom design, and for computed flow dynamic, and to enable proper output of 3D printing.

FIG. 4B depicts the illustration of a hollow model 420 generated after trimming, according to one example. The branching outline 412 is depicted as extending throughout the hollow model 420, but with portions of the hollow model that have the region shell cut X mm before the centerline endpoints. For example, the endpoint in branch 424 of the hollow model 420 may be trimmed to expose a large opening for the airway; whereas the endpoints in branches 426A, 426B, 426C of the hollow model 420 may be trimmed to expose small openings for the respective endpoints of the tree structure.

Figures 4C, 4D:
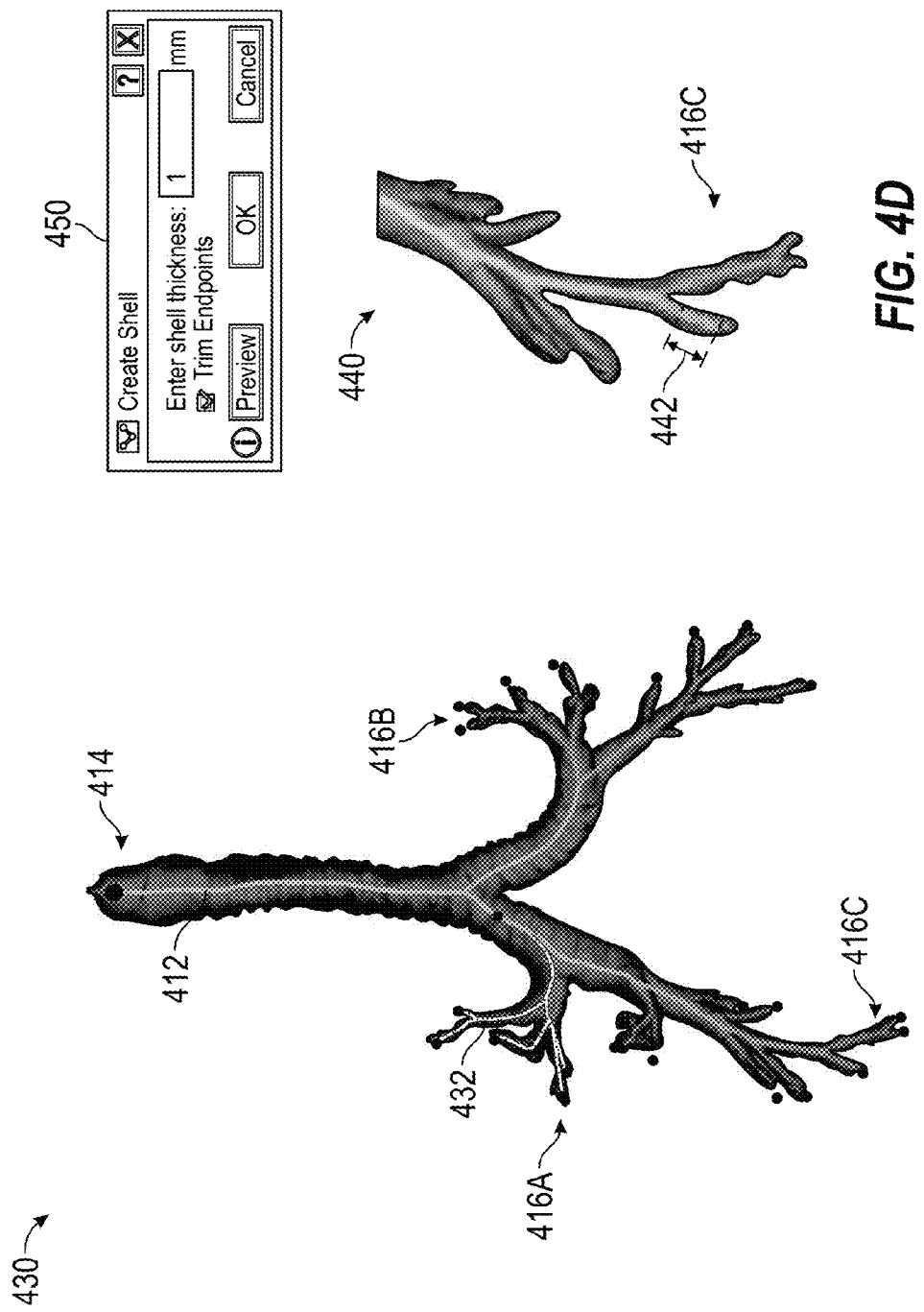

FIG. 4C depicts an illustration of a hollow model 430, based on the depiction of the hollow model 410 in FIG. 4A prior to trimming, but with the hollow model 430 including modifications to the selection of the branches to be trimmed. For example, the branch 416A is shown as being unselected (with a highlighted branch outline 432, such as may be depicted an alternate color or shading), whereas the outlines into the branches 416B, 416C remain selected.

The selection (or unselection) of respective branches may be implemented by receiving user interface inputs to designate such branches (such as by a user clicking on a particular branch to control whether the endpoints of the particular branch will or will not be trimmed). In an example, a default option may apply trimming to all endpoints of a branch outline. In another example, a user may accept or reject trimming of respective endpoints, or trimming of certain endpoints may be automatically controlled based on the type of anatomical structure being modeled. For example, a user may not intend to trim a cardiac apex when creating a hollow model of heart chambers.

FIG. 4D depicts a close-up illustration 440 of a portion of the branch 416C from the hollow model 410, 430 depicted in FIGS. 4A and 4C. This portion of the branch 416C is illustrated before clipping, with an illustration of a clipping portion 442 to be removed from the hollow model 410, 430. In the example of FIG. 4D, the clipping portion 442 corresponds to a selection value specified in a graphical user interface input 450, to "trim endpoints". The selections received in the graphical user interface input 450 may include a trim option (such as a check box whether to trim or not trim endpoints), and trim size (not shown, such as to trim X mm on centerline from selected endpoints).

An amount of the shell thickness to trim from an endpoint may correspond to an automatically determined value; or, the amount of the shell thickness to trim from an end point may correspond to user-input values or inputs. In another example, the amount of the shell thickness to trim for a proximal endpoint may be different from a distal endpoint, or fixed default values may be used for proximal and distal endpoints respectively.

Figure 5A:
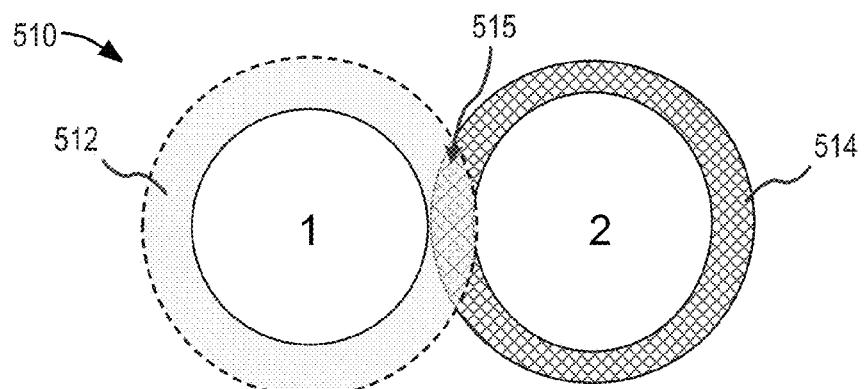
FIGS. 5A, 5B, and 5C illustrate respective visualizations of a region shell for a hollow model that are constrained for neighboring structures according to an example described herein.
Figure 5B:
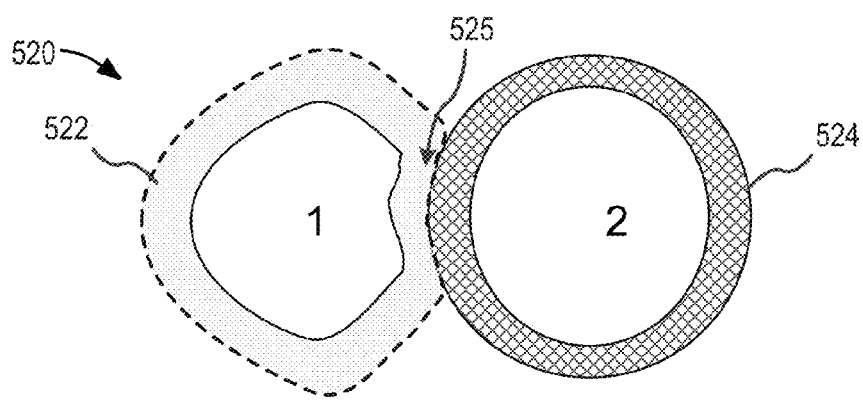
Figure 5C:
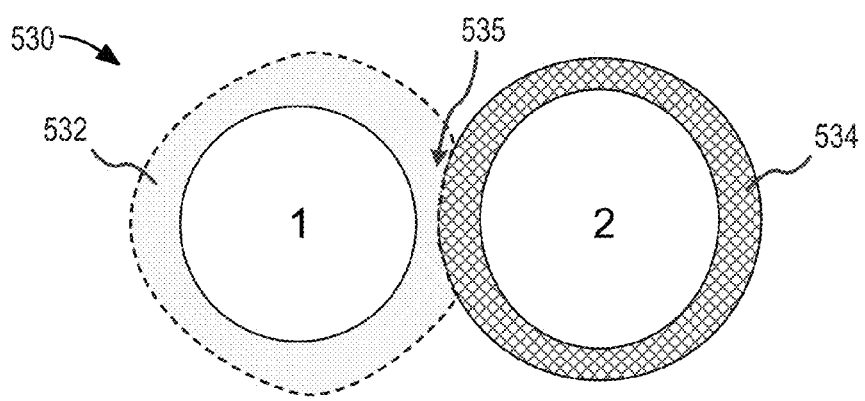

In a further example, the thickness or definition for the hollow model shell may be modified with constrained region generation techniques, such as to prevent interference or overlap with other shells or anatomical structures. FIGS. 5A, 5B, and 5C illustrate respective visualizations 510, 520, 530 of a region shell constrained for neighboring structures according to an example. In the following examples, a hollow shell model may be modified to prevent expansion in segmented region that conflicts with another region.

Growing a region shell in a contiguous structure may destroy a previous segmented structure, although growing the region into the source region may be acceptable to avoid a locally hollow shell. For example, FIG. 5A depicts the visualization 510 of a region shell generation where a first shell 512 of a hollow region 1 is partially contiguous with a second shell 514 of a hollow region 2. The contiguous region 515 conflicts, and growing the region shell of either the first shell 512 or the second shell 514 in a contiguous structure may destroy a previous segmented structure.

FIG. 5B depicts the visualization 520 of a modification to the region shell generation technique, to adapt to the contiguous structure conflict of FIG. 5A. As shown, the visualization 520 is provided for a scenario where the first shell 522 and the second shell 524 are resized to remove the contiguous conflict. Specifically, region 525 is adapted to reduce the size of the conflict in the region 525, by causing a change to the hollow shell to preserve the size of the hollow region 2 and the second shell 524, while reducing the size of the hollow region 1 to preserve the shell walls of the first shell 522.

FIG. 5C depicts the visualization 530 of a modification to the region shell generation, to adapt to the contiguous structure conflict of FIG. 5A. As shown, the visualization 530 is provided for a scenario where a region 535 is adapted to be not contiguous, where a normal thickness of a shell 532 would conflict in part with a shell 534. In the region 535, the shell 532 is configured to establish a locally reduced thickness in the conflict area, while preserving the source of the hollow region 1. (The region source of the hollow region 2 and the shell 534 are not affected).

These and other constraints may be used to generate or modify a shell, to ensure that certain structures are preserved, or to ensure that shell walls do not interfere with critical structures. A shell may be created or modified to be "thinner" because the mass of the region is subtracted from the dilated portion, or subtracted directly from a shell. Consequently, constraints of a hollow structure and neighboring structures (and neighboring shells) may be used to prevent any hollow model from conflicting with overlapping structures of interest.

In an example, a user interface control such as a checkbox may be used to define a hollow model constraint (and preserve the selected region or anatomical structure from interference). This user interface control, which may be provided from selecting a particular object that is constrained from a list of objects, may provide a constraint that a user can directly modify. Further, a user interface control such as a checkbox can also display a status to a user to easily determine which layers or structures are to be preserved during model generation.

Figure 6:
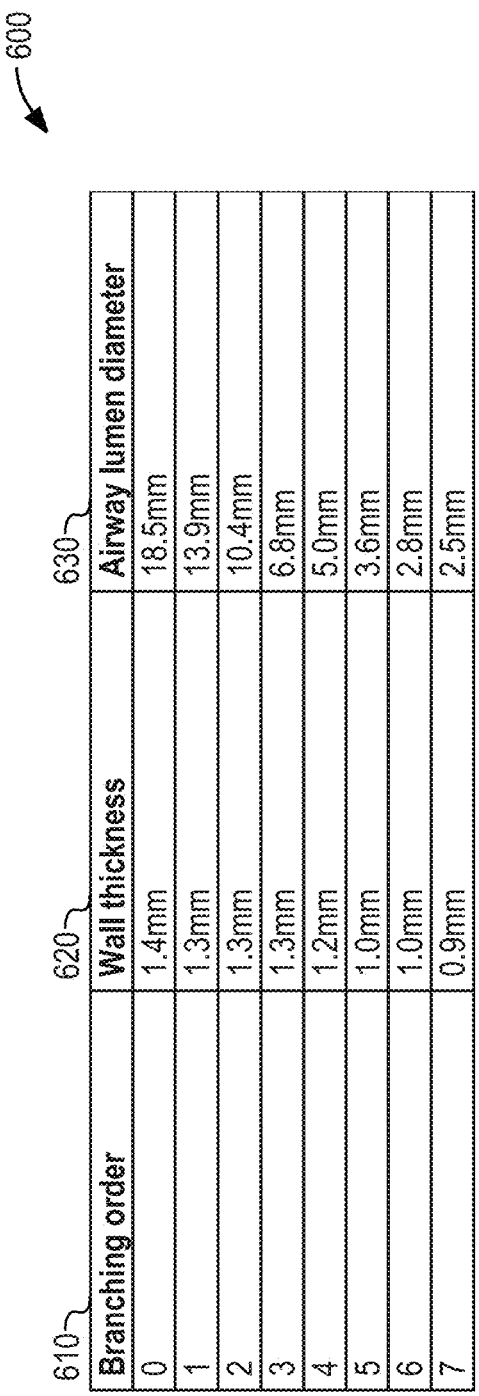
FIG. 6 illustrates respective values for defining variable thickness of a region shell for a hollow model according to an example described herein.

In a further example, the thickness or definition for a hollow model shell may be modified based on predefined modeling characteristics. A variable thickness for a shell wall of the airway structure may be determined and applied to a hollow model automatically or in response to user selection, depending on the type of branching or the anatomical structure being modeled. As result, the use of wall segmentation with variable thickness may be used to produce more realistic models for large vessel models or organ characteristics. FIG. 6 illustrates a chart 600 of respective values for defining variable thickness of a region shell of an airway structure according to an example described herein. For example, for lung airways, the thickness of a hollow model may be designed to resemble an airway wall shell that varies with airway branch generation characteristics.

The chart 600 depicted in FIG. 6 provides an illustration of a comparison of wall thickness 620 in comparison to lumen diameter 630. The typical wall thickness related to the branching order of the airway branch, with the branching order, follows Weibel's model. The computation of the variable wall thickness for the airways may be based upon a pre-computed branching order or the airway branch. In another example, the variable wall thickness may be based upon the local lumen diameter.

Additional examples of variable wall thickness for a lung bronchial structure are indicated in Montaudon et al., *Assessment of bronchial wall thickness and lumen diameter in human adults using multi-detector computed tomography: comparison with theoretical models*, Journal of Anatomy (2007), Vol. 211, pp. 577-588, which is incorporated by reference herein in its entirety. Accordingly, the thickness of a hollow airway model may be adjusted based on these and like findings.

As another example, the thickness of a hollow model may be designed to resemble a blood vessel, such as an artery or vein structure (e.g., coronaries). A simple way to compute the variable wall thickness changing with the local vessel diameter is to apply existing data from the human anatomy. A power law describes the relationship between the vessel diameter and wall thickness: $H=Ar^b$, with H: vessel wall thickness, for the well-studied coronaries, A=3.87. b=0.63 and r is the outer vessel radius.

Customized models may also be generated from a sample of vessel diameter and vessel wall thickness and fitting a similar power law using parametric curve fitting techniques.

For example, respective wall thickness values for an artery or vein may be defined based on a linear log-log relationship between arterial wall thickness (mm) and inner diameter (mm). Additional examples of variable wall thickness in arteries and veins are indicated in Guo et al., *Diameter-dependent axial prestretch of porcine coronary arteries and veins*, Journal of Applied Physiology, Vol. 112 no. 6, pp. 982-989, which is incorporated by reference herein in its entirety. Further, additional examples of existing data from human anatomy veins are indicated in Podesser et al., *Outer radius-wall thickness ratio, a postmortem quantitative histology in human coronary arteries*, Acta Anatomica 1998, Vol. 163, pp. 63-68.

A variable thickness modeling technique also may be used to create a shell wall that is modeled to become thinner as the shell extends from an anatomical point of interest or to provide a shell of smoothly varying thickness. For example, a modeled result may be produced from a modeling paradigm that starts with thicker elements, and becomes thinner moving in a distal/lateral direction. Such modeling may provide an enhancement to forms of simple generic wall segmentation, to assist generation of realistic models for large vessel models. Accordingly, variable thickness modeling techniques may be applicable to modeling of spaces for a segmented tubular structure such as arteries, veins, airways, bile ducts, or ureters, or for cavity organs such as a gallbladder, urinary bladder, stomach, heart, or colon.

In further example, the hollow model shell may be generated to include a plurality of layers that correspond to identified anatomical features. FIGS. 7A and 7B illustrate a depiction of layers of an anatomical structure used for defining variable thicknesses of a multi-layer region shell according to an example. For example, the simulation of biomimetic structures (such as artery walls) may include composite multi-layer structures.

FIG. 7A depicts a cut-out view of an artery wall structure, including a first layer 702 (e.g., corresponding to an adventitial layer), a second layer 704 (e.g., corresponding to a medial layer), and a third layer 706 (e.g., corresponding to an intimal layer). FIG. 7B depicts a cross-section view 720 of the artery wall structure, including the varying thicknesses for the first layer 702, second layer 704, and third layer 706 (indicated in the display of the thickness values 730 at a point of the vessel). For example, varying thicknesses may be produced from data of high resolution imaging modalities (e.g., CT scanners) that provide a high resolution export of data. Accordingly, imaging data may be used to model or provide a direct source of the thickness for a particular modeling of an anatomical structure.

FIG. 8 illustrates a graphical depiction 800 of multi-layer region shell generated from the artery wall structure of FIGS. 7A and 7B according to an example. As shown, the graphical depiction 800 includes an interior lumen 810 (the hollow space) surrounded by a third layer 802, a second layer 804, and a first layer 806. The graphical depiction may provide a representation of an approximation of the thickness presented at various portions of the artery wall structure, such as determined with the imaging techniques used to produce the cross-section view 720 in FIG. 7B.

In another example, the multiple layers (e.g., two or more layers) of an anatomical structure may be roughly defined using given ratios of thickness. These ratios and definitions may be adjusted and edited by a user in the graphical user interface as respective layers, or in response to automatic algorithms to match the anatomy as it appears in a source medical image.

The uses of a multilayer region shell may support a number of applications in bioprinting, realistic simulated vessels, airway modeling, and the like. The use of a multilayer region shell also provides a number of benefits for the control of 3D printing parts and metamaterial. Thus, the generation of the multiple layers, such as with the use of a 2- or 3-layer region option, may allow the printing of each part/layer with specific material properties. For example, a first layer may be created in a 3D printer with a soft material whereas the outer layer might be created in the 3D printer with a rigid material, to more correctly simulate the properties of the vessel or organ.

Figure 9:
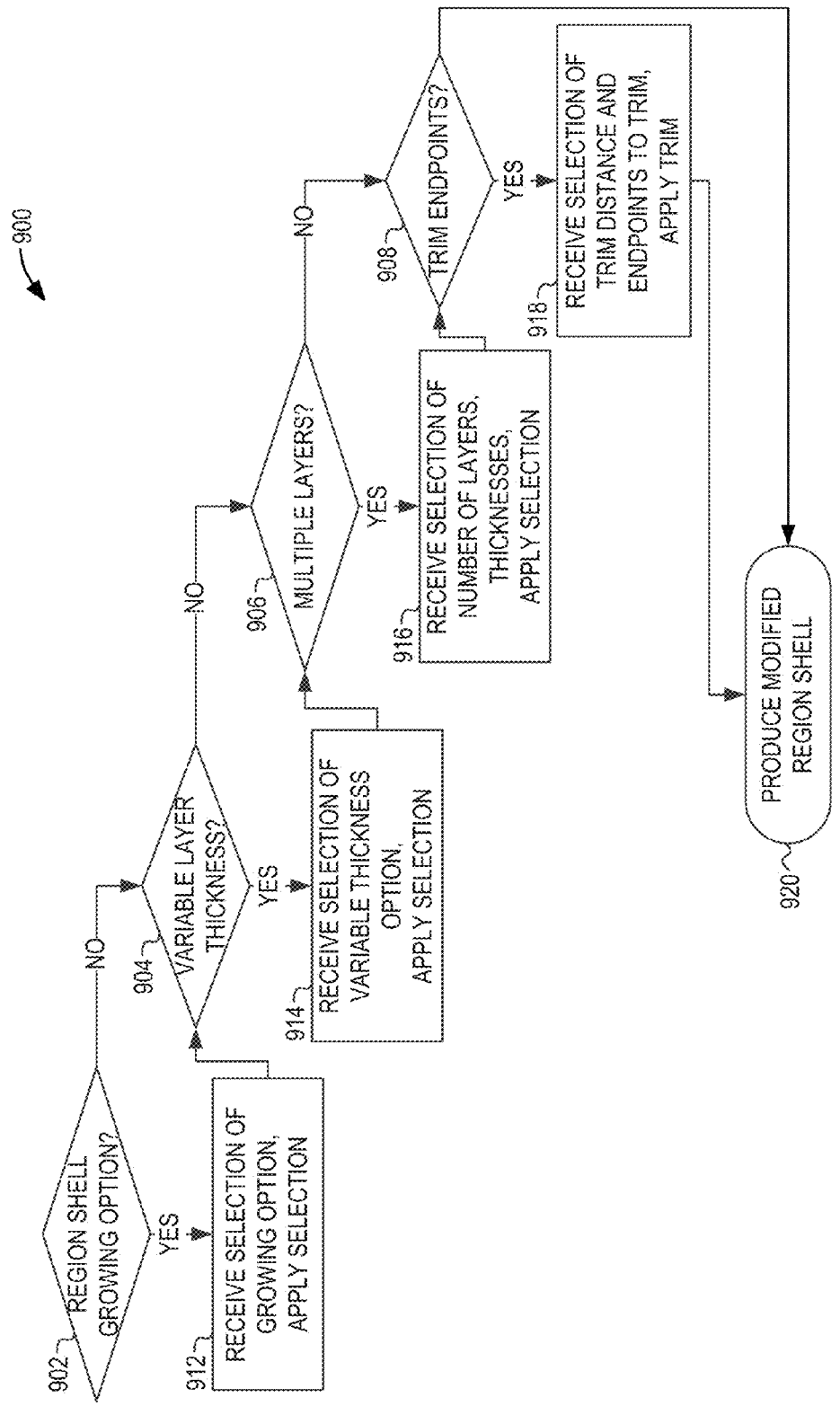
FIG. 9 illustrates a flowchart of a method for implementing region shell enhancements for a hollow model according to an example described herein.

FIG. 9 illustrates a flowchart 900 of a method for implementing region shell enhancements according to an example described herein. This flowchart 900 depicts the sequential application of the enhancements discussed above with reference to FIGS. 4A to 8. However, it will be understood that additional or fewer enhancements may be provided in such a method, and that such enhancements may be optional or user-controlled.

The flowchart 900 initially depicts an evaluation of whether to apply a region shell growing option (decision 902). If this option is selected or indicated, the visualization software may receive a user or automated selection of a shell growing option, and implement the selection or indication (operation 912). For example, this may include implementation of the operations described above with reference to FIGS. 5A, 5B, and 5C, including the generation or modification of region shells based on contiguous structure conflicts and whether to apply shell growing options into otherwise overlapping spaces.

The flowchart 900 further depicts an evaluation of whether to apply a variable layer thickness option (decision 904). If this option is selected or indicated, the visualization software may receive a user or automated selection of a variable thickness for the hollow model, and implement the selection or indication (operation 914). For example, this may include implementation of the operations described above with reference to FIG. 6, including the use of variable thickness values for a shell that is applied to model thicknesses of known anatomical features.

The flowchart 900 further depicts an evaluation of whether to apply a variable layer thickness option (decision 906). If this option is selected or indicated, the visualization software may receive a user or automated selection of a number of layers and thickness values for each of the layers for the hollow model, and implement the selection or indication (operation 916). For example, this may include implementation of the operations described above with reference to FIGS. 7A, 7B, and 8, including the definition of 2, 3, or more layers into a shell, and the generation of associated visualizations of such layers.

The flowchart 900 further depicts an evaluation of whether to apply endpoint trimming (decision 908). If this option is selected or indicated, the visualization software may receive a user or automated selection of endpoints in a tree structure of the model to preserve or to manually trim, and a user or automated selection of trim distance and the amount of data to trim, and implement the selections or indications (operation 918). For example, this may include implementation of the trimming operations described above with reference to FIGS. 4A, 4B, 4C, and 4D, including the processing of user input received in a graphical user interface to select or de-select certain branches of a tree, and trimming the endpoints of selected branches of the tree to defined dimensions.

As a result of the previous operations, a modified region shell may be produced (operation 920). This modified region shell may be generated for output as CAD-format data, or may be modeled further in an imaging visualization software application.

Figure 10A:
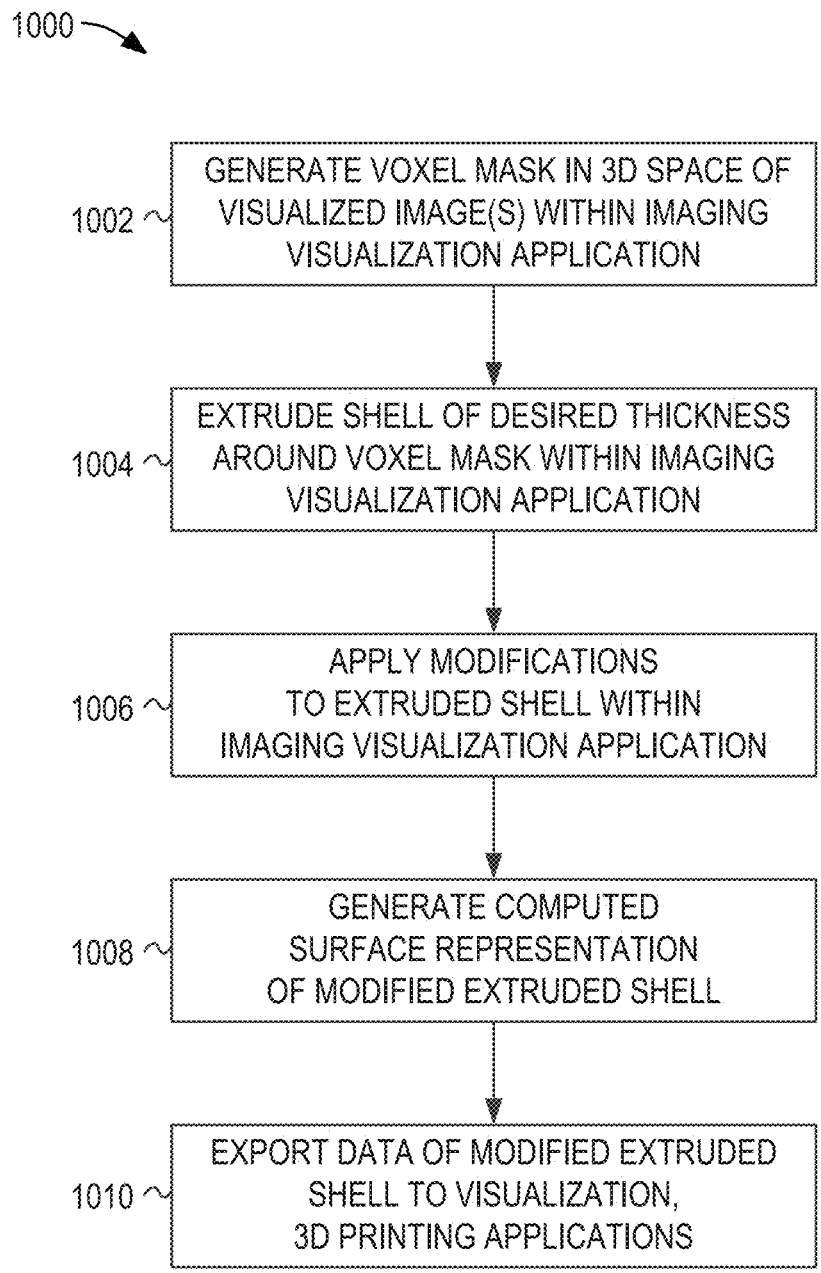
FIGS. 10A and 10B illustrate respective flowcharts of methods for generating hollow model data according to an example described herein.

FIG. 10A illustrates a flowchart 1000 of a method for generating hollow object model data according to an example. This flowchart 1000 provides a high-level depictions of operations used to generate the hollow object model data, but it will be understood that additional operations (including the integration of the operations from flowchart 900) may be optionally implemented into the depicted flow.

For example, the operations depicted in the flowchart 1000 include the generation of a voxel mask in a 3D space (operation 1002), such as from segmentation of a hollow object in a 3D space of one or more visualized images, provided in a medical imaging visualization application. A shell of desired thickness is extruded around the voxel mask (operation 1004), as this shell is generated within the 3D space that includes the contextual information of the medical image volume(s).

Modifications may be received and applied to the extruded shell (operation 1006), such as may occur in the medical imaging visualization application with user input of thickness modifications, the addition of multiple layers, or endpoint trimming (e.g., as depicted in the enhancement operations from the flowchart 900 of FIG. 9). After receiving the modification(s) to the shell, a computed surface representation of the modified extruded shell is generated (operation 1008). Data of the modified extruded shell (such as a mesh model) can then be exported to other visualization or 3D printing applications (operation 1010), in addition to output directly within the medical imaging visualization application.

Figure 10B:
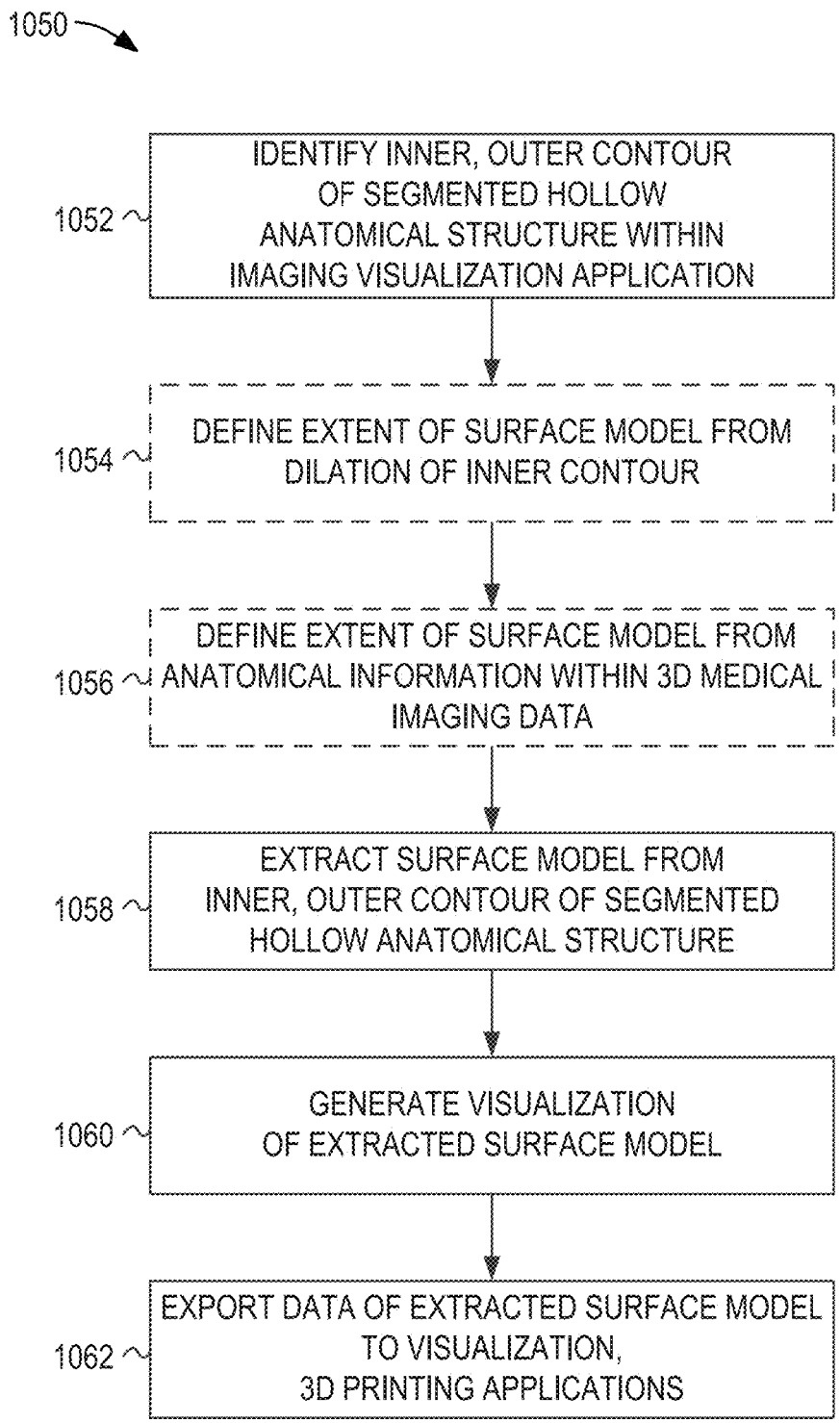

FIG. 10B illustrates a similar flowchart 1050 of a method for generating hollow object model data according to another example. However, FIG. 10B provides details of this method with use of contour-based surface model extraction. Again, the flowchart 1050 provides a high-level depictions of operations used to generate the hollow object model data, but it will be understood that additional operations (including the integration of the operations from flowchart 900) may be optionally implemented into the depicted flow.

The operations depicted in the flowchart 1050 include the identification of an inner contour and an outer contour from segmented hollow anatomical structure (operation 1052), such as from segmentation of a hollow object in a 3D space of one or more visualized images, within a medical imaging visualization application. A surface model is extracted from this inner and outer contour (operation 1058), based on one or more techniques which use the contextual information from the medical image volume(s). In a first example, the technique for extracting the surface model involves definition of the extent of the surface model using a dilation of an inner contour of the segmented hollow anatomical structure (operation 1054). In a second example, the technique for extracting the surface model involves definition of the extent of the surface model using the anatomical information directly within the 3D medical imaging data (operation 1056).

Similar to the discussion for FIG. 10A, modifications may be received and applied to the extracted surface model, such as may occur in the medical imaging visualization application with user input of thickness modifications, the addition of multiple layers, or endpoint trimming (e.g., as depicted in the enhancement operations from the flowchart 900 of FIG. 9). After receiving the modification(s) to the surface model, a computed visualization of the surface model is generated (operation 1060). Data of the modified extruded shell (such as a mesh model) can then be exported to other visualization or 3D printing applications (operation 1062), in addition to output directly within the medical imaging visualization application.

Figure 11:
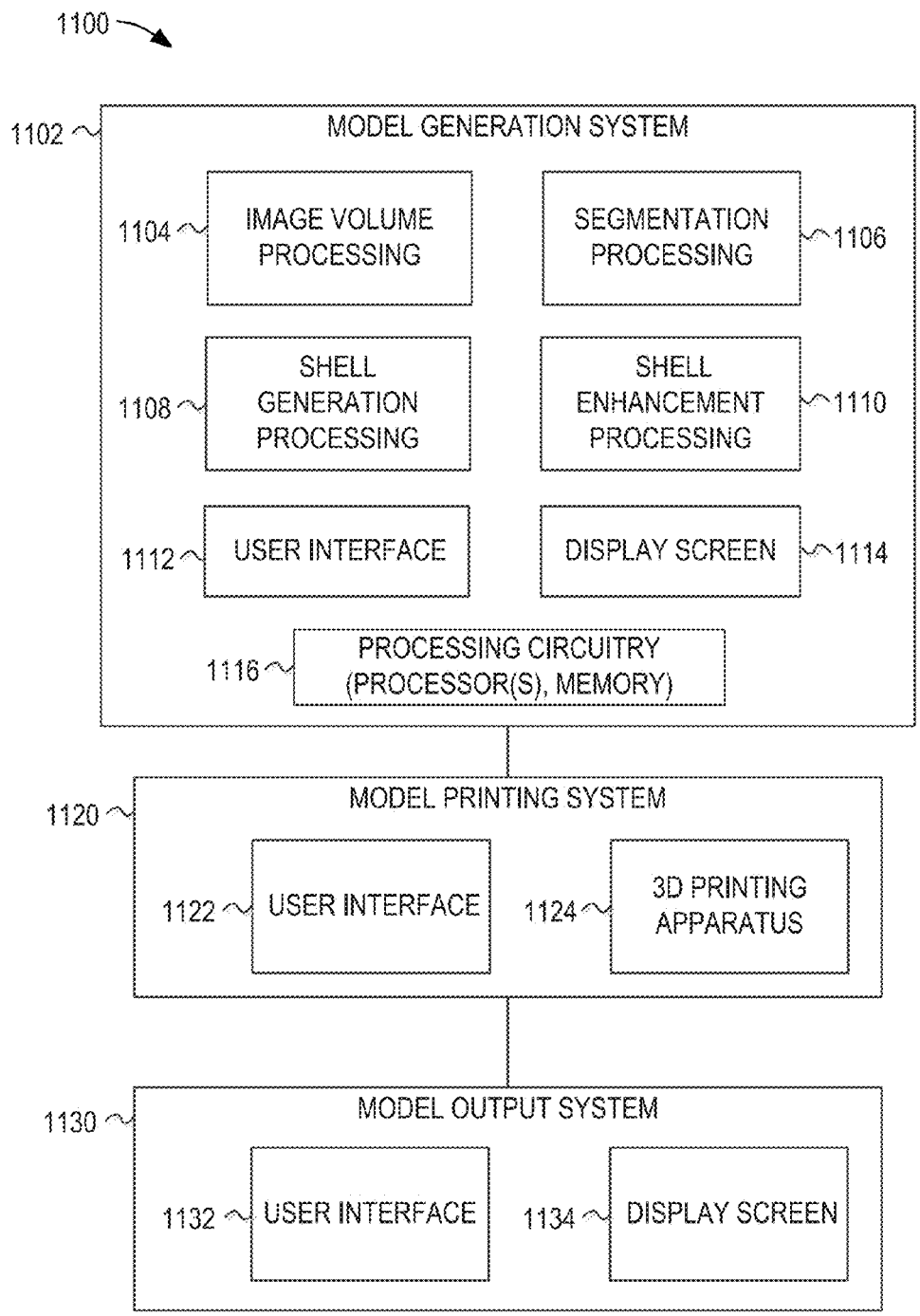
FIG. 11 illustrates a block diagram of components used in respective systems to generate, output, and print hollow model data for an object according to an example described herein.

FIG. 11 illustrates a block diagram 1100 of components used in respective systems to generate, output, and print model data for a hollow object according to an example described herein. For example, the systems may include: a model generation system 1102 configured to generate and modify the hollow model data using the techniques described herein; a model printing system 1120 configured to generate a physical output (e.g., a 3D print) of the hollow model data using the techniques described herein; and a model output system 1130 configured to generate a virtual output (e.g., a computer display) of the hollow model data using the techniques described herein.

The model generation system 1102 may include processing circuitry 1116, a display screen 1114, a user interface 1112, and model processing components (including image volume processing 1104, segmentation processing 1106, shell generation processing 1108, and shell enhancement processing 1110). In an example, the model processing components 1104, 1106, 1108, 1110 and the user interface 1112 may be provided from specialized hardware operating independent from the processor and the memory; in other examples, the model processing components 1104, 1106, 1108, 1110 may be software-configured hardware that is implemented with use of the processor and the memory or other aspects of the processing circuitry 1116 (e.g., by instructions executed by the processor and the memory). In a further example, the user interface 1112 and the display screen 1114 are used to engage the model processing components 1104, 1106, 1108, 1110 with use of the processing circuitry 1116, to generate and modify a hollow model using the techniques described herein.

The model printing system 1120 may include a user interface 1122 and a 3D printing apparatus 1124, with the user interface 1122 used to control or affect operation of the 3D printing apparatus 1124. For example, the 3D printing apparatus 1124 may be configured to receive, process, and output a 3D physical representation of the hollow model, based on hollow model data produced by the model generation system 1102.

The model output system 1130 may include a user interface 1132 and a display screen 1134, with the user interface 1132 used to control or affect the display of a visualization of the hollow model via the display screen 1134 (including the output of CAD-based perspectives of the hollow model, as generated from the model generation system 1102). In another example, the features of the model output system 1130 may be integrated or combined with the features of the model generation system 1102 or the model printing system 1120.

Figure 12:
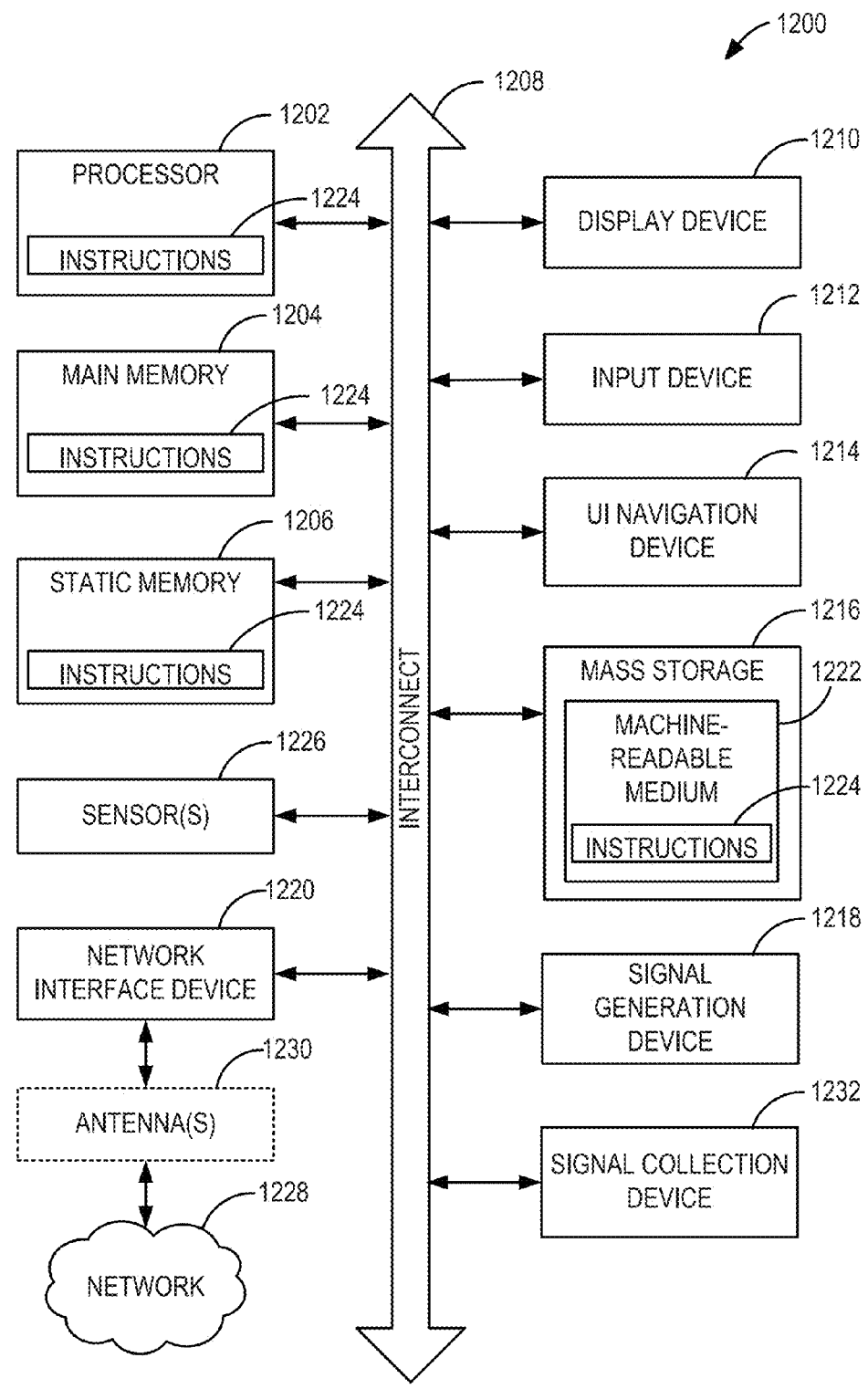
FIG. 12 illustrates an example of a machine configured to perform computing or electronic processing operations according to an example described herein.

FIG. 12 is a block diagram illustrating an example computing system machine upon which any one or more of the methodologies herein discussed may be run. Computer system 1200 may be embodied as a computing device, providing operations of the components featured in the various figures, including components of the medical imaging system 108, visualization computer system 110, the model generation system 1102, the model printing system 1120, the model output system 1130, or as an execution platform for the operations in flowcharts 200, 900, or 1000 or the graphical user interfaces 300*a*, 300*b*, 300*c*, 300*d*, or any other processing, storage, or computing platform or component described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The computer system machine may be a personal computer (PC) that may or may not be portable (e.g., a notebook or a netbook), a tablet, a Personal Digital Assistant (PDA), a mobile telephone or smartphone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 1200 includes a processor 1202 (e.g., a central processing unit (CPU), a graphics processing unit (GPU) or both), a main memory 1204 and a static memory 1206, which communicate with each other via an interconnect 1208 (e.g., a link, a bus, etc.). The computer system 1200 may further include a video display unit 1210, an alphanumeric input device 1212 (e.g., a keyboard), and a user interface (UI) navigation device 1214 (e.g., a mouse). In one embodiment, the video display unit 1210, input device 1212 and UI navigation device 1214 are a touch screen display. The computer system 1200 may additionally include a storage device 1216 (e.g., a drive unit), a signal generation device 1218 (e.g., a speaker), a signal collection device 1232, and a network interface device 1220 (which may include or operably communicate with one or more antennas 1230, transceivers, or other wireless communications hardware), and one or more sensors 1226.

The storage device 1216 includes a machine-readable medium 1222 on which is stored one or more sets of data structures and instructions 1224 (e.g., software) embodying or utilized by any one or more of the methodologies or functions described herein. The instructions 1224 may also reside, completely or at least partially, within the main memory 1204, static memory 1206, and/or within the processor 1202 during execution thereof by the computer system 1200, with the main memory 1204, static memory 1206, and the processor 1202 also constituting machine-readable media.

While the machine-readable medium 1222 is illustrated in an example embodiment to be a single medium, the term "machine-readable medium" may include a single medium or multiple media (e.g., a centralized or distributed database, and/or associated caches and servers) that store the one or more instructions 1224. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, optical media, and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1224 may further be transmitted or received over a communications network 1228 using a transmission medium via the network interface device 1220 utilizing any one of a number of well-known transfer protocols (e.g., HTTP). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Other applicable network configurations may be included within the scope of the presently described communication networks. Although examples were provided with reference to a local area wireless network configuration and a wide area Internet network connection, it will be understood that communications may also be facilitated using any number of personal area networks, LANs, and WANs, using any combination of wired or wireless transmission mediums.

The embodiments described above may be implemented in one or a combination of hardware, firmware, and software. While some embodiments described herein illustrate only a single machine or device, the terms "system", "machine", or "device" shall also be taken to include any collection of machines or devices that individually or jointly execute a set (or multiple sets) of instructions to perform any one or more of the methodologies discussed herein.

Examples, as described herein, may include, or may operate on, logic or a number of components, modules, or mechanisms. Such components may be tangible entities (e.g., hardware) capable of performing specified operations and may be configured or arranged in a certain manner. In an example, circuits may be arranged (e.g., internally or with respect to external entities such as other circuits) in a specified manner to implement such components. In an example, the whole or part of one or more computer systems (e.g., a standalone, client or server computer system) or one or more hardware processors may be configured by firmware or software (e.g., instructions, an application portion, or an application) that operates to perform specified operations. In an example, the software may reside on a machine readable medium. In an example, the software, when executed by the underlying hardware, causes the hardware to perform the specified operations.

Accordingly, such components may be a tangible entity that is physically constructed, specifically configured (e.g., hardwired), or temporarily (e.g., transitorily) configured (e.g., programmed) to operate in a specified manner or to perform part or all of any operation described herein. Considering examples in which such components are temporarily configured, each of the components need not be instantiated at any one moment in time. For example, where the components comprise a general-purpose hardware processor configured using software, the general-purpose hardware processor may be configured as respective different components at different times. Software may accordingly configure a hardware processor, for example, to constitute a particular components at one instance of time and to constitute a different component at a different instance of time.

Additional examples of the presently described method, system, and device embodiments are suggested according to the structures and techniques described above and specified in the following claims. For example, the subject matter described herein may be embodied by a method performed by a client (e.g., user-controlled) device (e.g., a computer system) for generating a hollow model from medical image data within a visualization software application, the software application executed by a computing device having at least one processor and at least one memory, and the method implemented by electronic operations performed using the processor and the memory.

As another example, the subject matter described herein may be embodied by a method performed by a server device (e.g., a remote computer system or computerized service) for generating a hollow model from medical image data to support operations of a client visualization software application, the software application executed by a computing device having at least one processor and at least one memory, and the method implemented by electronic operations performed using the processor and the memory.

As yet another example, the subject matter described herein may be embodied by a non-transitory machine-readable medium, the machine-readable medium including instructions, which when executed by a machine having a hardware processor, causes the machine to perform operations of the client- or server-performed method(s).

As yet another example, the subject matter described herein may be embodied by a hollow model generation system, comprising: processing circuitry including at least one processor and at least one memory; a display screen; a user interface output with the display screen; and features to generate a hollow model via the user interface using the operations described herein.

As yet another example, the subject matter described herein may be embodied by a hollow model output system, comprising: processing circuitry including at least one processor and at least one memory; a display screen; a user interface output with the display screen; and features to output a visualization of a hollow model via the user interface using the operations described herein.

As yet another example, the subject matter described herein may be embodied by a hollow model printing system, comprising: processing circuitry including at least one processor and at least one memory; a 3D printing apparatus under the control of the processor and memory; a user interface to operate the 3D printing apparatus; and instructions executed with the processor and the memory to perform the 3D printing of a hollow model with the 3D printing apparatus, the hollow model being produced using the operations described herein.

Other non-limiting examples may be configured to operate separately, or can be combined in any permutation or combination with any one or more of the other examples provided above, in the following claims, or throughout the present disclosure.

What is claimed is:

1. A method for generating a hollow model from a medical image, performed by operations executed within a medical imaging visualization application of a computing device, the computing device having at least one processor and at least one memory, with the operations comprising:
generating a voxel mask from an interior space of a segmented anatomical structure, wherein the segmented anatomical structure is produced from three-dimensional medical imaging data provided to the medical imaging visualization application;
extruding, within the medical imaging visualization application, a shell mask of a defined thickness from the voxel mask, wherein extruding the shell mask of the defined thickness includes generating a dilated voxel mask from the voxel mask and removing the voxel mask from the dilated voxel mask; and
generating a visualization of the extruded shell mask, the visualization of the extruded shell mask adapted to be displayed with a graphical user interface of the medical imaging visualization application;
wherein the shell mask is modified to remove a binary mask of another anatomical structure used in the medical imaging visualization application if the binary mask of the another anatomical structure includes a fixed external structure, and
wherein the shell mask is modified to update the binary mask of the another anatomical structure to exclude the shell mask if the binary mask of the another anatomical structure does not include a fixed external structure.

2. The method of claim 1, the operations comprising:
previewing the shell mask in the graphical user interface of the medical imaging visualization application, including:
generating a first graphical preview of the shell mask in a first display in the graphical user interface, wherein the first graphical preview provides a three-dimensional representation of the shell mask; and
generating a second graphical preview of the shell mask in a second display in the graphical user interface, wherein the second graphical preview provides an overlay of the shell mask on a source medical image,
wherein the source medical image is a two-dimensional representation of a three-dimensional image acquired using a computed tomography (CT), magnetic resonance imaging (MRI), 3D X-ray angiography, or 3D ultrasound modality.

3. The method of claim 1, the operations comprising:
receiving, in the graphical user interface of the medical imaging visualization application, a user-specified value to specify the defined thickness for the shell mask; and
displaying a three-dimensional representation of the visualization of the extruded shell mask in the graphical user interface of the medical imaging visualization application.

4. The method of claim 3, the operations comprising:
exporting data that represents the extruded shell mask from the medical imaging visualization application, wherein the exported data defines a mesh model of the shell mask; and
wherein the visualization of the extruded shell mask displayed in the graphical user interface of the medical imaging visualization application is produced from the mesh model of the shell mask.

5. The method of claim 1, the operations comprising:
generating the segmented anatomical structure by performing segmentation on an image volume that provides the three-dimensional medical imaging data; and
receiving a selection of the segmented anatomical structure in the graphical user interface of the medical imaging visualization application, wherein the generating of the voxel mask from the interior space of the segmented anatomical structure is performed in response to the selection of the segmented anatomical structure.

6. The method of claim 1, wherein the dilated voxel mask is generated by supersampling to create a finer resolution for voxels of the dilated voxel mask than a resolution of the voxel mask.

7. The method of claim 1, wherein the segmented anatomical structure includes a tubular tree structure, and the operations comprising:
   trimming endpoints of the tubular tree structure by modifying selected extremities of the tubular tree structure in the shell mask, wherein the tubular tree structure is modified by:
      generating a tree from a plurality of centerlines of the segmented anatomical structure;
      computing endpoints of the tree from the plurality of centerlines; and
      removing portions of the shell mask located within a determined distance from the endpoints of the tree.

8. The method of claim 1, wherein extruding the shell mask of the defined thickness includes, for a portion of the shell mask having a thickness that interferes with a neighboring anatomical structure:
   reducing the thickness of the portion of the shell mask; or
   reducing the interior space of the segmented anatomical structure to preserve the thickness of the portion of the shell mask.

9. The method of claim 1,
   wherein extruding the shell mask of the defined thickness includes defining a plurality of layers in the shell mask, and
   wherein thicknesses of respective layers of the plurality of layers in the shell mask are established from respective user-specified values or system-determined values corresponding to the segmented anatomical structure.

10. The method of claim 1,
    wherein the defined thickness is variable within the shell mask to include a plurality of thicknesses, and
    wherein the plurality of thicknesses are determined from defined anatomic relationships of anatomical wall thicknesses and inner diameter values of the segmented anatomical structure.

11. At least non-transitory machine-readable medium, the machine-readable medium including instructions, which when executed by a machine having a hardware processor, causes the machine to perform operations that:
    generate, within a medical imaging visualization application, a voxel mask from an interior space of a segmented anatomical structure, wherein the segmented anatomical structure is segmented from a three-dimensional medical image by the medical imaging visualization application;
    extrude, within the medical imaging visualization application, a shell mask of a defined thickness from the voxel mask;
    extrude the shell mask of the defined thickness with a generation of a dilated voxel mask from the voxel mask using supersampling and a removal of the voxel mask from the dilated voxel mask; and
    generate, within the medical imaging visualization application, a visualization of the shell mask for output with a graphical user interface of the medical imaging visualization application;
    wherein the shell mask is modified to remove a binary mask of another anatomical structure used in the medical imaging visualization application if the binary mask of the another anatomical structure includes a fixed external structure; and
    wherein the shell mask is modified to update the binary mask of the another anatomical structure to exclude the shell mask if the binary mask of the another anatomical structure does not include a fixed external structure.

12. The machine-readable medium of claim 11, the medium further including instructions that cause the machine to perform operations that:
    previewing the shell mask in the graphical user interface of the medical imaging visualization application, including:
       generating a first graphical preview of the shell mask in a first display in the graphical user interface, wherein the first graphical preview provides a three-dimensional representation of the shell mask; and
       generating a second graphical preview of the shell mask in a second display in the graphical user interface, wherein the second graphical preview provides an overlay of the shell mask on a source medical image,
       wherein the source medical image is a two-dimensional representation of the three-dimensional medical image, wherein the three-dimensional medical image is acquired using a computed tomography (CT), magnetic resonance imaging (MRI), 3D X-ray angiography, or 3D ultrasound modality.

13. The machine-readable medium of claim 11, the medium including instructions that cause the machine to perform operations that:
    receive, in the graphical user interface of the medical imaging visualization application, a user-specified value to specify the defined thickness for the shell mask; and
    display a three-dimensional representation of the visualization of the extruded shell mask in the graphical user interface of the medical imaging visualization application.

14. The machine-readable medium of claim 13, the medium including instructions that cause the machine to perform operations that:
    export data that represents the extruded shell mask from the medical imaging visualization application, wherein the exported data defines a mesh model of the shell mask; and
    wherein the visualization of the extruded shell mask displayed in the graphical user interface of the medical imaging visualization application is produced from the mesh model of the shell mask.

15. The machine-readable medium of claim 11, the medium including instructions that cause the machine to perform operations that:
    generate the segmented anatomical structure by performing segmentation on an image volume that provides data for the three-dimensional medical image; and
    receive a selection of the segmented anatomical structure of the three-dimensional medical image in the graphical user interface of the medical imaging visualization application, wherein generation of the voxel mask from the interior space of the segmented anatomical structure is performed in response to the selection of the segmented anatomical structure.

16. The machine-readable medium of claim 11, wherein the segmented anatomical structure includes a tubular tree structure; the medium including instructions that cause the machine to perform operations that:

trim endpoints of the tubular tree structure by modifying selected extremities of the tubular tree structure in the shell mask, wherein the tubular tree structure is modified by:
- generation of a tree from a plurality of centerlines of the segmented anatomical structure;
- computation of endpoints of the tree from the plurality of centerlines; and
- removal of portions of the shell mask located within a determined distance from the endpoints of the tree.

17. The machine-readable medium of claim 11, the medium including instructions that cause the machine to perform operations that, for a portion of the shell mask having a thickness that interferes with a neighboring anatomical structure:
- reduce the thickness of the portion of the shell mask; or
- reduce the interior space of the segmented anatomical structure to preserve the thickness of the portion of the shell mask.

18. The machine-readable medium of claim 11, the medium including instructions that cause the machine to perform operations that:
- extrude the shell mask of the defined thickness by definition of a plurality of layers in the shell mask;
- wherein thicknesses of respective layers of the plurality of layers in the shell mask are established from respective user-specified values or system-determined values corresponding to the segmented anatomical structure.

19. The machine-readable medium of claim 11, the medium including instructions that cause the machine to perform operations that:
- establish the defined thickness as variable within the shell mask to include a plurality of thicknesses;
- wherein the plurality of thicknesses are determined from defined anatomic relationships of anatomical wall thicknesses and inner diameter values of the segmented anatomical structure.

20. A system, comprising:
a medical imaging processing system, comprising processing circuitry having at least one processor and at least one memory, the processing circuitry to:
- generate a voxel mask from an interior space of a segmented anatomical structure, the segmented anatomical structure being produced from three-dimensional medical imaging data of a DICOM image volume;
- extrude a shell mask of a defined thickness from the voxel mask;
- extrude the shell mask of the defined thickness with a generation of a dilated voxel mask from the voxel mask using supersampling and a removal of the voxel mask from the dilated voxel mask;
- generate data that represents the extruded shell mask, wherein the data defines a mesh model of the shell mask;
- generate a visualization of the extruded shell mask to be output with a graphical user interface of a medical imaging visualization application, wherein the visualization of the extruded shell mask is a three-dimensional visualization produced from the mesh model of the shell mask;
- modify the shell mask to remove a binary mask of another anatomical structure used in the medical imaging visualization application if the binary mask of the another anatomical structure includes a fixed external structure; and
- modify the shell mask to update the binary mask of the another anatomical structure to exclude the shell mask if the binary mask of the another anatomical structure does not include a fixed external structure.

21. The system of claim 20, further comprising:
a three-dimensional printer to receive the data that represents the shell mask and generate a physical representation of the mesh model of the shell mask.

\* \* \* \* \*